United States Patent [19]

Huger et al.

[11] Patent Number: 5,776,955
[45] Date of Patent: Jul. 7, 1998

[54] USE OF UNSUBSTITUTED AND SUBSTITUTED N-(PYRROL-1-YL) PYRIDINAMINES AS ANTICONVULSANT AGENTS

[75] Inventors: Francis Parker Huger, Milford; Craig Paul Smith, Hillsborough; Sathapana Kongsamut, Madison; Lei Tang, Princeton, all of N.J.

[73] Assignee: Hoechst Marion Roussel, Inc.

[21] Appl. No.: 676,608

[22] Filed: Jul. 8, 1996

Related U.S. Application Data

[60] Provisional application No. 60/045,789, Jul. 27, 1995.

[51] Int. Cl.$^6$ ............................................. A61K 31/44
[52] U.S. Cl. ................................... 514/343; 514/339
[58] Field of Search ................................. 514/339, 343

[56] References Cited

U.S. PATENT DOCUMENTS

| | | | |
|---|---|---|---|
| 4,868,190 | 9/1989 | Effland et al. | 514/278 |
| 4,880,822 | 11/1989 | Effland et al. | 514/339 |
| 4,970,218 | 11/1990 | Effland et al. | 514/339 |
| 5,032,599 | 7/1991 | Effland et al. | 514/343 |
| 5,053,511 | 10/1991 | Effland et al. | 546/15 |
| 5,179,099 | 1/1993 | Effland et al. | 514/278 |
| 5,296,488 | 3/1994 | Effland et al. | 514/278 |
| 5,356,910 | 10/1994 | Kongsamut et al. | 514/339 |

FOREIGN PATENT DOCUMENTS

| | | |
|---|---|---|
| 0287982 | 10/1988 | European Pat. Off. . |
| 0376155 | 7/1990 | European Pat. Off. . |

OTHER PUBLICATIONS

Tang, L. et al, Effects of besipirdine at the voltage–dependent sodium channel:, British Journal of Pharmacology (Nov., 1995) 116, pp. 2468–2472.

*Primary Examiner*—Kimberly Jordan
*Attorney, Agent, or Firm*—Balaram Gupta; Barbara E. Kurys

[57] ABSTRACT

This invention relates to a method of treating a patient in need of relief from convulsions which comprises administering to such a patient a convulsion-alleviating amount of a compound of the formula

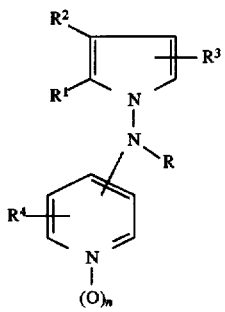

wherein R, $R^1$, $R^2$, $R^3$, $R^4$, m and n are as defined within.

76 Claims, No Drawings

USE OF UNSUBSTITUTED AND SUBSTITUTED N-(PYRROL-1-YL) PYRIDINAMINES AS ANTICONVULSANT AGENTS

This application claims the benefit of Provisional Application Ser. No. 60/045,789, filed Jul. 27, 1995.

BACKGROUND OF THE INVENTION

Certain 2,3-dihydro-1-pyridinylamino)-indoles have been disclosed as having utility for the treatment of memory dysfunction characterized by cholinergic deficit as well as anticonvulsant and analgesic utility (for example, see U.S. Pat. Nos. 5,179,099 and 5,296,488). In addition, certain N-(pyrrol-1-yl)pyridinamines, including certain compounds within the scope of the present invention, have been disclosed as having utility for enhancing memory (for example, see U.S. Pat. No. 5,032,599). Furthermore, certain N-(pyridinyl)-1H-indol-1-amines, including certain compounds within the scope of the present invention, have been disclosed as having utility for the treatment of obsessive compulsive disorders (for example, see U.S. Pat. No. 5,356, 910), for the enhancement of memory (for example, see U.S. Pat. Nos. 4,880,822 and 4,970,218), and as analgesic and antidepressant agents (for example, see U.S. Pat. No. 4,880, 822).

SUMMARY OF THE INVENTION

This invention relates to a method of treating a patient in need of relief from convulsion which comprises administering to such a patient a convulsion-alleviating amount of a compound of the formula

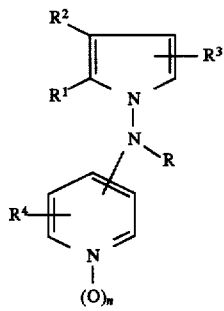

wherein

R is hydrogen, $(C_1-C_6)$alkyl, $(C_2-C_6)$alkenyl, $(C_2-C_6)$ alkynyl or phenyl$(C_1-C_6)$alkyl;

$R^1$ is hydrogen, halogen or $(C_1-C_6)$alkyl;

$R^2$ is hydrogen, halogen or $(C_1-C_6)$alkyl; or $R^1$ and $R^2$ taken together with the carbons to which they are attached form a benzene ring fused to the pyrrole ring wherein the benzene ring is optionally substituted by one or two substituents independently selected from the group of halogen, $(C_1-C_6)$alkyl, $(C_1-C_6)$alkoxy, aryl $(C_1-C_6)$alkoxy, hydroxy, nitro, amino, $(C_1-C_6)$alkylamino or di $(C_1-C_6)$ alkylamino;

$R^3$ is hydrogen, halogen or $(C_1-C_6)$alkyl;

$R^4$ is hydrogen, halogen, amino or $(C_1-C_6)$alkyl;

n is 0 or 1; or a pharmaceutically acceptable acid addition salt thereof.

Throughout the specification and the appended claims, a given chemical formula or name shall encompass all stereo, optical, and geometrical isomers thereof where such isomers exist, as well as pharmaceutically acceptable acid addition salts thereof and solvates thereof such as, for example, hydrates.

The following general rules of terminology shall apply throughout the specification and the appended claims.

Unless otherwise stated or indicated, the term $(C_1-C_6)$ alkyl denotes a straight or branched alkyl group having from 1 to 6 carbon atoms. Examples of $(C_1-C_6)$alkyl include methyl, ethyl, n-propyl, iso-propyl, n-butyl, iso-butyl, sec-butyl, t-butyl and straight- and branched-chain pentyl and hexyl.

Unless otherwise stated or indicated, the term $(C_1-C_6)$ alkoxy denotes a straight or branched alkoxy group having from 1 to 6 carbon atoms. Examples of $(C_1-C_6)$alkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term $(C_2-C_6)$ alkenyl denotes a straight or branched alkenyl group having from 1 to 6 carbon atoms. Examples of $(C_2-C_6)$alkenyl include, for example, vinyl, allyl, 1-propenyl, 2-methyl-3-butenyl, 3-methyl-1-butenyl, 2-methyl-2-butenyl and the like.

Unless otherwise stated or indicated, the term $(C_2-C_6)$ alkynyl denotes a straight or branched alkynyl group having from 2 to 6 carbon atoms. Examples of $(C_2-C_6)$alkynyl include acetylenyl, propargyl, 1-propynyl, 2-methyl-3-butynyl, 3-methyl-1-butynyl, 2-methyl-2-butynyl and the like.

Unless otherwise stated or indicated, the term halogen shall mean fluorine, chlorine, bromine or iodine.

In a preferred embodiment of the invention the patient in need of relief from convulsion is treated with a compound of the formula

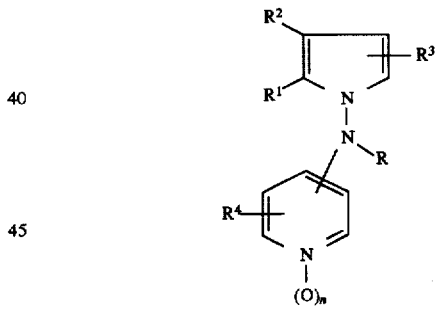

wherein

R is hydrogen, $(C_1-C_6)$alkyl, $(C_2-C_6)$alkenyl, $(C_2-C_6)$ alkynyl or phenyl$(C_1-C_6)$alkyl;

$R^1$ is hydrogen, halogen or $(C_1-C_6)$alkyl;

$R^2$ is hydrogen, halogen or $(C_1-C_6)$alkyl;

$R^3$ is hydrogen, halogen or $(C_1-C_6)$alkyl;

$R^4$ is hydrogen, halogen, amino or $(C_1-C_6)$alkyl;

n is 0 or 1; or a pharmaceutically acceptable acid addition salt thereof.

Preferably $R^2$ and $R^3$ are hydrogen, $R^4$ is hydrogen or $(C_1-C_6)$alkyl and n is 0.

In another preferred embodiment of the invention the patient in need of relief from convulsion is treated with a compound of the formula

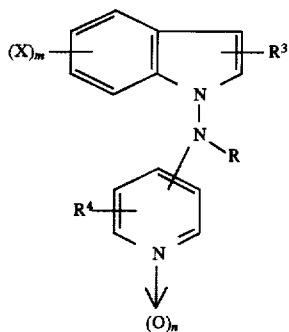

wherein

R is hydrogen, (C$_1$-C$_6$)alkyl, (C$_2$-C$_6$)alkenyl, (C$_2$-C$_6$)alkynyl or phenyl(C$_1$-C$_6$)alkyl;

R$^3$ is hydrogen, halogen, (C$_1$-C$_6$)alkyl or (CH$_2$)$_z$NH$_2$;

R$^4$ is hydrogen, halogen, amino or (C$_1$-C$_6$)alkyl; X is hydrogen, halogen, (C$_1$-C$_6$)alkyl, (C$_1$-C$_6$)alkoxy, aryl (C$_1$-C$_6$)alkoxy, hydroxy, nitro, amino, (C$_1$-C$_6$)alkylamino or di (C$_1$-C$_6$)alkylamino;

m is 1 or 2;

n is 0 or 1; and z is 1 or 2; or a pharmaceutically acceptable acid addition salt thereof.

Preferably X is hydrogen, R$^3$ is hydrogen or methyl, R$^4$ is hydrogen or fluoro and n is 0.

The compounds of Formula I used in the method of this invention can be prepared by utilizing the synthetic scheme described below where the parameters R, R$^1$, R$^2$, R$^3$, R$^4$, X, m, n and z have the respective meanings as defined above unless otherwise indicated.

STEP A

An N-aminopyrrole of Formula II is allowed to react with a chloro- or fluoropyridine of Formula III (where X is chlorine or fluorine) to afford a compound of Formula Ia.

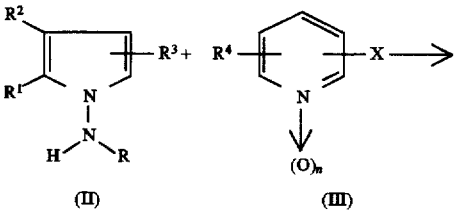

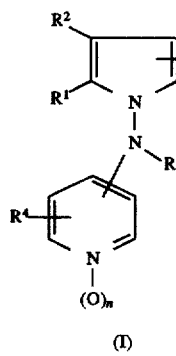

The reaction is typically carried out in an organic solvent such as bis(2-methoxy-ethyl)ether, diethyl ether, dimethyl ether, dioxane, tetrahydrofuran dimethylformamide, dimethylacetamide, N-methyl-2-pyrrolidone, hexamethylphosphoramide, dimethylsulfoxide, ethanol, isopropanol and the like at a temperature of between about 20° C. and 150° C.

STEP B

As an alternative to STEP A, a compound of Formula Ib obtained above is allowed to react with a strong base such as sodium hydride or potassium hydride in a suitable solvent such as a polar aprotic solvent including, for example, dimethylformamide, dimethylsulfoxide and ethereal solvents or an aromatic hydrocarbon at a temperature of between about –10° C. and 50° C., preferably between about 0° C. and –25° C. to form the corresponding nitrogen anion and the latter is allowed to react with a loweralkyl chloride or bromide of the formula R-Hal (where Hal is chlorine or bromide and R is loweralkyl) or a diloweralkyl sulfate of the formula (RO)$_2$SO$_2$ at a temperature of between about –10° C. and 80° C., preferably between 0° C. and 25° C., to afford the compound of Formula Ia where R is loweralkyl.

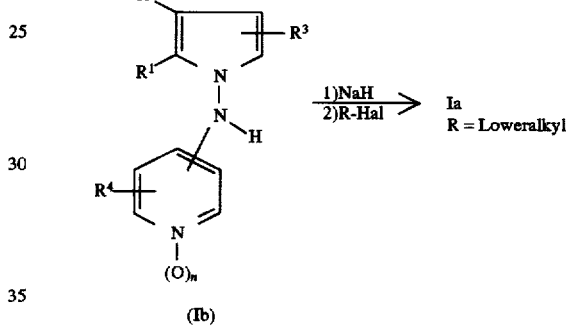

STEP C

As an alternative to STEP A, when R$^3$ is hydrogen or (C$_1$-C$_6$)alkyl and R$^1$ and R$^2$ are hydrogen, (C$_1$-C$_6$)alkyl or halogen, compound I can be obtained by reacting a compound of Formula IV with a compound of Formula V.

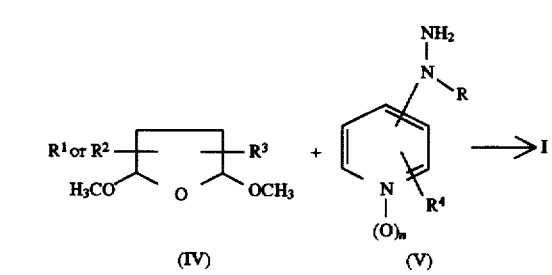

The reaction is typically conducted in an alkanoic acid, preferably lower alkanoic acid such as, for example, glacial acetic acid, propanoic acid or formic acid at a temperature of from about 80° to about 120° C.

STEP D

Where R$^1$ and R$^2$ taken together with the carbons to which they are attached form a benzene ring fused to the pyrrole ring to form a compound of Formula VI

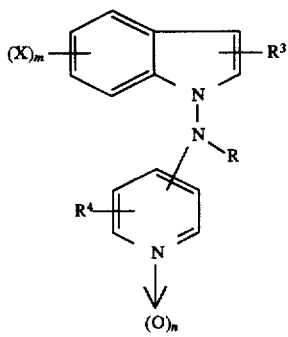

(VI)

where X is amino, $(C_1-C_6)$alkylamino or di$(C_1-C_6)$ alkylamino, a compound obtained from STEP A or STEP B having the appropriate substituents except for X and X is nitro, is converted to the amino or alkylamino group using reduction methods known in the art.

STEP E

Where compounds of Formula VI where X is hydroxy are desired, a compound obtained from STEP A or STEP B having the appropriate substituents except for X and X is benzyloxy, is converted to the corresponding hydroxy compound in a routine manner known in the art.

STEP F

Where compounds of Formula I where $R^4$ is amino are desired, a compound obtained from STEP A or STEP B having the appropriate substituents except for $R^4$ and $R^4$ is nitro is converted to the corresponding amino compound in a manner known in the art.

STEP G

Where compounds of Formula I where the nitrogen is in the 3-position of the pyridine ring and $R^4$ is hydrogen are desired, a compound obtained from STEP A or STEP B having the appropriate substituents except for $R^4$ and $R^4$ is halogen substituted at the 5-position of the pyridine ring is converted to the corresponding compound where $R^4$ is hydrogen in a manner known in the art.

Compounds I of the instant invention are useful as anticonvulsant agents due to their anticonvulsant activity in mammals. Anticonvulsant potential is measured by inhibition of [$^3$H]batrachotoxin binding in vitro, and anticonvulsant activity is measured using the Supramaximal Electroshock Test in the male mouse.

INHIBITION OF [$^3$H]BATRACHOTOXIN (BTX) BINDING TO BRAIN MENBRANE SODIUM CHANNELS

PURPOSE:

This assay was established to determine the direct effect of test compounds on the binding of [$^3$H]batrachotoxin to sodium channels in a membrane preparation from rat brain. It has been shown that the alkaloid batrachotoxin binds to a unique site (site II) of the neuronal membrane sodium channel to activate the voltage-sensitive sodium channel (Catterall, 1980). Furthermore, it is now known that certain anticonvulsant agents, such as diphenylhydantoin and carbamazepine, allosterically inhibit the binding of [$^3$H] batrachotoxin to membrane sodium channels (Willow and Catterall, 1982; Olsen, 1986).

METHODS:

Vesicular preparations of male Wistar rat cortices were used for the binding assay. Briefly, the rat brain was removed and the cortex was separated and placed in a glass homogenizer filled with 2 ml ice-cold Krebs buffer. The tissue was homogenized at 3,500 rpm for 6 up and down strokes, and centrifuged at 1,000 g for 15 minutes. The supernatant was discarded and the pellet was resuspended in binding medium (130 mM choline chloride, 5.5 mM glucose, 0.8 mM $MgSO_4$, 5.4 mM KCl and 50 mM HEPES, pH 7.4). Incubations were carried out in a total volume of 250 ul containing 1 µM tetrodotoxin, 0.02 mg of scorpion venom, 25 nM [$^3$H]batrachotoxin, approximately 400 µg of protein of the vesicular preparation and various concentrations of the test compound. After 60 minutes incubation at 25° C., the reaction was terminated by diluting with 3 ml of wash medium (163 mM choline chloride, 1.8 mM $CaCl_2$, 0.8 mM $MgSO_4$ and 5 mM HEPES, pH 7.4) and collecting under vacuum on a glass-fiber filter. The filters were then washed twice with 3 ml of wash medium and placed in scintillation vials with 5 ml of Esocint (National Diagnostics). The tritium content was measured by scintillation spectroscopy. Non-specific binding of [$^3$H]batrachotoxin was determined in the presence of 300 µM vetratridine and was determined to be 4.75±0.15% of the total binding.

DRUGS

Drugs were dissolved in 50 mM HEPES buffer, pH 7.4, or dissolved in ethanol and diluted in 50 mM HEPES buffer, pH 7.4.

REFERENCES

1. Catterall, W. A. (1980): Neurotoxins that act on voltage-sensitive sodium channels in excitable membranes. Ann. Rev. Pharmacol. Toxicol. 20, 15–43.
2. Willow, M. and Catterall, W. A. (1982): Inhibition of binding of [$^3$H]batrachotoxinin A 20--benzoate to sodium channels by the anticonvulsant drugs diphenylhydantoin and carbamazepine. Mol. Pharmacol. 22, 627–635.
3. Olsen, R. W. (1986): Convulsant and anticonvulsant drug receptor binding. In: Receptor Binding in Drug Research. (R. A. O'Brien, ed.) Marcel Dekker, New York, 1986, pp. 93–123.

TABLE I

Inhibition of [$^3$H]Batrachotoxin Binding

| COMPOUND | $IC_{50}$ (µM) |
| --- | --- |
| N-(n-Propyl)-N-(4-pyridinyl)-1H-indol-1-amine HCl | 5 |
| N-(3-fluoro-4-pyridinyl)-3-methyl-N-propyl-1H-indol-1-amine HCl [also known as N-(n-Propyl)-N-(3-fluoro-4-pyridinyl)-1H-3-methylindol-1-amine HCl] | 31 |
| (Reference Compound) Carbamazepine | 94 |
| N-(4-pyridinyl)-1H-indol-1-amine | 18 |
| N-(1-methylethyl)-N-(4-pyridinyl)-1H-indol-1-amine | 9 |
| N-(2-methylpropyl)-N-(4-pyridinyl)-1H-indol-1-amine | 9 |
| 5-bromo-N-(4-pyridinyl)-1H-indol-1-amine | 23 |
| 5-bromo-N-propyl-N-(4-pyridinyl)-1H-indol-1-amine | 14 |

TABLE I-continued

Inhibition of [³H]Batrachotoxin Binding

| COMPOUND | IC$_{50}$ (μM) |
|---|---|
| N-(3-chloro-4-pyridinyl)-1H-indol-1-amine | 14 |
| N-(3-chloro-4-pyridinyl)-N-propyl-1H-indol-1-amine | 32 |
| 4-[N-(1H-indol-1-yl)]-3,4-pyridinamine | 22 |
| N-(3-methyl-4-pyridinyl)-1H-indol-1-amine | 21 |
| 3-chloro-N-(4-pyridinyl)-1H-indol-1-amine | 11 |
| 3-chloro-N-propyl-N-(4-pyridinyl)-1H-indol-1-amine | 10 |
| 3-methyl-N-(4-pyridinyl)-1H-indol-1-amine | 11 |
| 3-ethyl-N-methyl-N-(4-pyridinyl)-1H-indol-1-amine | 12 |
| 3-aminomethyl-N-propyl-N-(4-pyridinyl)-1H-indol-1-amine | 10 |
| 3-aminoethyl-N-(4-pyridinyl)-1H-indol-1-amine | 44 |
| 1-[propyl-4-(3-fluoropyridinyl)amino]-1H-indol-5-ol | 70 |
| 3-methyl-1-(4-pyridinylamino)-1H-indol-5-ol | 20 |
| 3-methyl-1-(propyl-4-pyridinylamino)-1H-indol-5-ol | 21 |
| N-(3-chloro-4-pyridinyl)-3-methyl-1H-indol-1-amine | 29 |
| N-(3-chloro-4-pyridinyl)-3-methyl-N-propyl-1H-indol-1-amine | 44 |
| N-(3-fluoro-4-pyridinyl)-3-methyl-1H-indol-1-amine | 42 |
| 3-methyl-1-[propyl-(3-fluoro-4-pyridinyl)amino]-1H-indol-5-ol | 19 |
| N-(3-pyridinyl)-1H-indol-1-amine | 12 |
| N-(2-pyridinyl)-1H-indol-1-amine | 12 |
| N-(1H-pyrrol-1-yl)-4-pyridinamine | 40 |
| N-ethyl-N-(1H-pyrrol-1-yl)-4-pyridinamine | 86 |
| N-propyl-N-(1H-pyrrol-1yl)-4-pyridinamine | 66 |
| 3-fluoro-N-propyl-N-(1H-pyrrol-1yl)-4-pyridinamine | 46 |

SUPRAMAXIMAL ELECTROSHOCK IN MICE

PURPOSE

This procedure is used as to predict anticonvulsant activity of a test compound in vivo by its ability to block a full tonic seizure induced by a supramaximal electroshock stimulation as an indication of efficacy in preventing grand mal seizures.

METHODS

Male CD-1 mice (Charles River) weighing 18–30 grams were housed in accordance with the "NIH Guide to Care and Use of Laboratory Animals" (National Institutes of Health Care Publication 85-23, revised 1985) with a 12 hour light/dark cycle and free access to food and water. On the day of testing, animals are brought to the laboratory and randomly assigned to groups of six for the time course experiments and to test groups of ten for the dose-response experiments.

The apparatus used for the test was the Wahlquist Electroshock Stimulator (Model H), which has a power source of 120 volts ac. A current of 15.5 mA lasting for 300 msec was delivered by placing the terminals of the stimulator across the eyes of the animal. This stimulus results in a tonic seizure, defined as a brief period of hindlimb flexion followed by a prolonged period of hindlimb extension. A compound is considered to give protection if the mouse does not exhibit extensor tonus, which can be defined as the hindlimb extension portion of the seizure. Protection is calculated as a normalized percent inhibition relative to a vehicle treated control group.

A time course is performed to determine the peak time of drug action and then a dose response performed at the peak time to determine drug potency. Mice are dosed in a randomized fashion using a total of 4 dose groups and one vehicle control group. The ED$_{50}$ value and 95% confidence limits are calculated by a computerized Litchfield and Wilcoxon analysis.

DRUGS

Drugs are prepared dissolved in distilled water and, if insoluble a drop of surfactant is added. Drugs are routinely administered intraperitoneally for this test and given in a dosage volume of 10 ml/kg.

REFERENCES

1. Woodbury, L. A. and Davenport, V. P. (1952): Design and use of a new electroshock seizure apparatus and analysis of factors altering seizure threshold and pattern. *Arch. Int. Pharmacodyn.* 92, 97–107.

TABLE II

INHIBITION OF SUPRAMAXIMAL ELECTROSHOCK IN MICE

| COMPOUND | ED$_{50}$ (mg/kg) |
|---|---|
| N-(n-Propyl)-N-(4-pyridinyl)-1H-indol-1-amine HCl | 14.2 |
| N-(3-Fluoro-4-pyridinyl)-1H-3-methyl-N-(n-propyl)-indol-1-amine HCl [also known as N-(n-Propyl)-N-(3-fluoro-4-pyridinyl)-1H-3-methylindol-1-amine HCl] | 50% @ 30 and 60 mpk |
| 3-Methyl-N-(4-pyridinyl)-1H-indol-1-amine oxalate [also known as N-(4-pyridinyl)-1H-3-methylindol-1-amine oxalate] | 13 |
| 3-Methyl-N-propyl-N-(4-pyridinyl)-1H-indol-1-amine maleate [also known as N-(n-Propyl)-N-(4-pyridinyl)-1H-3-methylindol-1-amine maleate] | 14.4 |
| N-(2,5-Dimethyl-1H-pyrrol-1-yl)-N-(n-propyl)-4-pyridinamine Maleate (Reference Compounds) | 50.1 |
| Diphenylhydantoin | 9.4 |
| Carbamazepine | 18.6 |

Effective quantities of the compounds of this invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form in capsule, it may contain, in addition to material of the above type, a liquid carrier such as a fatty oil. Other dosage unit forms may contain other various materials which modify the physical form of the dosage unit, for example, as coatings. Thus, tablets or pills may be coated with sugar, shellac or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 5–300 milligrams of active compound.

The solutions or suspensions may also include the following components: a sterile diluent such as water for injection, saline solution, fixed oils, polyethylene glycols, glycerine, propylene glycol or other synthetic solvents, antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparations can be enclosed in disposable syringes or multiple dose vials made of glass or plastic.

Examples of the compounds of this invention include:
N-(1H-Pyrrol-1-yl)-4-pyridinamine
N-Methyl-N-(1H-pyrrol-1-yl)-4-pyridinamine
N-Ethyl-N-(1H-pyrrol-1-yl)-4-pyridinamine
N-Propyl-N-(1H-pyrrol-1-yl)-4-pyridinamine
N-Phenylmethyl-N-(1H-pyrrol-1-yl)-4-pyridinamine
N-(Butyl)-N-(1H-pyrrol-1-yl)-4-pyridinamine
N-(2-Propenyl)-N-(1H-pyrrol-1-yl)-4-pyridinamine
N-(2-Propynyl)-N-(1H-pyrrol-1-yl)-4-pyridinamine
N-(2-Chloro-1H-pyrrol-1-yl)-N-methyl-4-pyridinamine
N-(2-Chloro-1H-pyrrol-1-yl)-N-ethyl-4-pyridinamine
N-(2-Chloro-1H-pyrrol-1-yl)-N-propyl-4-pyridinamine
N-(2-Chloro-1H-pyrrol-1-yl)-4-pyridinamine
2-Butyl-N-methyl-N-(1H-pyrrol-1-yl)-4-pyridinamine
N-(2-Ethyl-1H-pyrrol-1-yl)-N-methyl-4-pyridinamine
N-Methyl-N-(2-propyl-1H-pyrrol-1-yl)-4-pyridinamine
N-(4-Pyridinyl)-1H-indol-1-amine
N-Methyl-N-(4-pyridinyl)-1H-indol-1-amine
N-Ethyl-N-(4-pyridinyl)-1H-indol-1-amine
N-Propyl-N-(4-pyridinyl)-1H-indol-1-amine
5-Methoxy-N-propyl-N-(4-pyridinyl)-1H-indol-1-amine
3-Ethenyl-N-methyl-N-(4-pyridinyl)-1H-indol-1-amine
3-Ethyl-N-methyl-N-(4-pyridinyl)-1H-indol-1-amine
5-Chloro-N-(4-pyridinyl)-1H-indol-1-amine
5-Chloro-N-propyl-N-(4-pyridinyl)-1H-indol-1-amine
5-Bromo-N-(4-pyridinyl)-1H-indol-1-amine
5-Bromo-N-methyl-N-(4-Pyridinyl)-1H-indol-1-amine
5-Bromo-N-propyl-N-(4-pyridinyl)-1H-indol-1-amine
5-Nitro-N-(4-pyridinyl)-1H-indol-1-amine
N-Methyl-5-nitro-N-(4-pyridinyl)-1H-indol-1-amine
3-Methyl-N-(4-pyridinyl)-1H-indol-1-amine
3-Methyl-N-propyl-N-(4-pyridinyl)-1H-indol-1-amine
N-(3-Fluoro-4-pyridinyl)-3-methyl-1H-indol-1-amine
N-(3-Fluoro-4-pyridinyl)-3-methyl-N-propyl-1H-indol-1-amine
N-(3-Fluoro-4-pyridinyl)-N-propyl-1H-indol-1-amine
2-Methyl-N-(4-pyridinyl)-1H-indol-1-amine
N-(3-Methyl-4-pyridinyl)-1H-indol-1-amine
N-(3-Methyl-4-pyridinyl)-N-propyl-1H-indol-1-amine
N-(3-Fluoro-4-pyridinyl-1H-indol-1-amine
N-(3-Chloro-4-pyridinyl)-1H-indol-1-amine
N-(3-(Fluoro-4-pyridinyl)-2-methyl-1H-indol-1-amine
N-(3-Chloro-4-pyridinyl)-3-methyl-1H-indol-1-amine
N-Propyl-N-(4-pyridinyl)-3-ethenyl-1H-indol-1-amine
3-Ethyl-N-propyl-N-(4-pyridinyl)-1H-indol-1-amine
N-Butyl-N-(4-pyridinyl)-1H-indol-1-amine
N-(2-Propynyl)-N-(4-pyridinyl)-1H-indol-1-amine
N-(2-Methylpropyl)-N-(4-pyridinyl)-1H-indol-1-amine
N-Pentyl-N-(4-pyridinyl)-1H-indol-1-amine
N-(1-Methylpropyl)-N-(4-pyridinyl)-1H-indol-1-amine
N-(1-Methylethyl)-N-(4-pyridinyl)-1H-indol-1-amine
2-Methyl-N-propyl-N-(4-pyridinyl)-1H-indol-1-amine
N-(3-Fluoro-4-pyridinyl)-N-(2-propenyl)-3-methyl-1H-indol-1-amine
N-(3-Chloro-4-pyridinyl)-N-propyl-1H-indol-1-amine
N-(3-Fluoro-4-pyridinyl)-N-(2-propynyl)-1H-indol-1-amine
N-(3-Fluoro-4-pyridinyl)-3-methyl-N-(2-propynyl)-1H-indol-1-amine
N-(3-Fluoro-4-pyridinyl)-2-methyl-N-propyl-1H-indol-1-amine
N-(3-Chloro-4-pyridinyl)-3-methyl-N-propyl-1H-indol-1-amine
N-(3-Fluoro-4-pyridinyl)-N-(2-propenyl)-1H-indol-1-amine
4-[N-(1H-indol-1-yl)]-3,4-pyridinamine,
3-chloro-N-(4-pyridinyl)-1H-indol-1-amine,
3-chloro-N-propyl-N-(4-pyridinyl)-1H-indol-1-amine,
3-aminomethyl-N-propyl-N-(4-pyridinyl)-1H-indol-1-amine,
3-aminoethyl-N-(4-pyridinyl)-1H-indol-1-amine, 1-[propyl-4-(3-fluoropyridinyl)amino]-1H-indol-5-ol,
3-methyl-1-(4-pyridinylamino)-1H-indol-5-ol,
3-methyl-1-(propyl-4-pyridinylamino)-1H-indol-5-ol,
3-methyl-1-[propyl-(3-fluoro-4-pyridinyl)amino]-1H-indol-5-ol,
N-(3-pyridinyl)-1H-indol-1-amine,
N-(2-pyridinyl)-1H-indol-1-amine,
N-(2,5-dimethyl-1H-pyrrol-1-yl)-N-(n-propyl)-4-pyridinamine, or
3-fluoro-N-propyl-N-(1H-pyrrol-1-yl)-4-pyridinamine.

The following examples are presented in order to illustrate the synthesis of various compounds which can be used for the method of this invention.

EXAMPLE 1

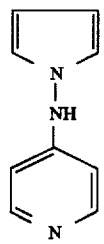

N-(1H-Pyrrol-1-yl)-4-pyridinamine

A solution of 4-chloropyridine (15 g) and N-aminopyrrole (18 g) in 225 ml of diglyme was stirred at 150° C. for one hour and thereafter cooled, diluted with water and basified with sodium carbonate. The mixture was extracted with ethyl acetate, and the organic extract was dried over anhydrous magnesium sulfate, filtered and evaporated to an oil. This oil was purified by high performance liquid chromatography (HPLC hereafter) using silica gel and ethyl acetate to give 12 g of a solid, m.p. 150° C. Five grams of the solid was recrystallized twice from benzene to give 2.8 g of crystals, m.p. 153°–154° C.

ANALYSIS:

Calculated for $C_9H_9N_3$: 67.90%C 5.70%H 26.40%N Found: 67.53%C 5.81%H 26.18%N

EXAMPLE 2

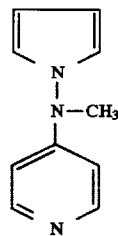

N-Methyl-N-(1H-pyrrol-1-yl)-4-pyridinamine hydrochloride

To an ice-cooled suspension containing 1.5 g of sodium hydride in 5 ml of dimethylformamide was slowly dropped a solution of N-(1H-pyrrol-1-yl)-4-pyridinamine (4 g) in 10 ml of dimethylformamide. After the initial brisk hydrogen evolution subsided, the reaction mixture was slowly warmed to ambient temperature and thereafter warmed at 50° C. for thirty minutes. The reaction mixture was again cooled with an ice bath and a solution of dimethyl sulfate (3.8 g) in 5 ml of dimethylformamide was slowly added.

After thirty minutes, the reaction mixture was stirred with 300 ml of ice water and extracted with dichloromethane. The organic extract was washed with water and saturated sodium chloride solution and thereafter dried over anhydrous magnesium sulfate, filtered and evaporated to 4 g of an oil. This oil was purified by HPLC (silica gel, ethyl acetate) to give 3.5 g of an oil. This oil was dissolved in 10 ml of warm isopropanol and filtered, and thereafter converted to the hydrochloride salt by the addition of ethereal hydrogen chloride. The crystals which formed upon cooling were collected and dried to give 3.1 g of crystals, m.p. 226°–227° C. These crystals were sublimed at 135°–150° C. @ 0.01 mm Hg to give 2.9 g of crystals, m.p. 226°–227° C.

ANALYSIS:

Calculated for $C_{10}H_{11}N_3 \cdot HCl$: 57.28%C 5.77%H 20.04%N Found: 57.39%C 5.78%H 19.99%N

EXAMPLE 3

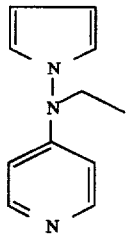

N-Ethyl-N-(1H-pyrrol-1-yl)-4-pyridinamine hydrochloride

A solution of N-(1H-pyrrol-1-yl)-4-pyridinamine (4 g) in 20 ml of dimethylformamide was slowly added dropwise to an ice-cooled suspension containing 1.2 g of sodium hydride in 5 ml of dimethylformamide. After the initial brisk reaction subsided, the mixture was stirred cold for thirty minutes, and thereafter a solution of diethyl sulfate (4.3 g) in 10 ml of dimethylformamide was added. After stirring twenty hours at ambient temperature, the reaction mixture was quenched with 500 ml of water and extracted with dichloromethane. The organic extract was washed with water and saturated sodium chloride solution and thereafter dried over anhydrous magnesium sulfate, filtered and evaporated to 4.3 g of an oil. This oil was purified by HPLC (silica, ethyl acetate) to give 3.7 g of an oil. This oil was dissolved in 10 ml of warm isopropanol, filtered, and acidified by the addition of ethereal hydrogen chloride. The product which formed upon cooling was collected and dried to give 3.3 g of a solid, m.p. 224°–225° C.

ANALYSIS:

Calculated for $C_{11}H_{13}N_3 \cdot HCl$: 59.06%C 6.31%H 18.79%N Found: 58.84%C 6.52%H 18.61%N

EXAMPLE 4

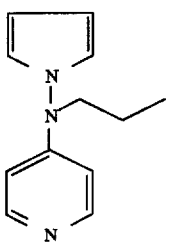

N-Propyl-N-(1H-pyrrol-1-yl)-4-pyridinamine hydrochloride

A solution of N-(1H-pyrrol-1-yl)-4-pyridinamine (3 g) in 25 ml of dimethylformamide was slowly dropped into a suspension containing 1 g of sodium hydride in 5 ml of dimethylformamide. After the anion formation, the reaction mixture was cooled with an ice bath and a solution of 1-bromopropane (2.8 g) in 5 ml of dimethylformamide was slowly added. After stirring one hour, the reaction mixture was quenched with water and extracted with dichloromethane. The organic extract was washed with water and saturated sodium chloride solution, and thereafter dried over anhydrous magnesium sulfate, filtered and evaporated to an oil. This oil was purified by flash chromatography (silica, ethyl acetate) to give 5 g of an oil. This oil was converted to the hydrochloride salt in warm isopropanol. The crystals which formed upon dilution with ether were collected and dried to give 3.3 g of a solid, m.p. 230° C.–232° C. (dec.). This material was recrystallized from isopropanol-ether to give 2.6 g of crystals, m.p. 232°–233° C. (decomposition, hereafter "dec.").

ANALYSIS:

Calculated for $C_{12}H_{15}N_3 \cdot HCl$: 60.62%C 6.78%H 17.68%N Found: 60.70%C 6.88%H 17.67%N

EXAMPLE 5

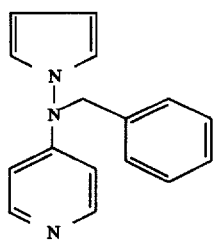

N-Phenylmethyl-N-(1H-pyrrol-1-yl)-4-pyridinamine hydrochloride

A solution of N-(1H-pyrrol-1-yl)-4-pyridinamine (4 g) in 20 ml of dimethylformamide was slowly added to an ice-cooled stirred suspension containing 1.1 g of sodium hydride in 5 ml of dimethylformamide. After the anion formation, a solution of benzylbromide (4.7 g) in 10 ml of dimethyl formamide was slowly added. After stirring thirty minutes, the reaction mixture was stirred with 500 ml of ice water and extracted with ether. The organic extract was washed with water and saturated sodium chloride solution thereafter and dried over anhydrous magnesium sulfate, filtered and evaporated to 6 g of an oil. This material was purified by flash chromatography (silica, ethyl acetate) to give 4.4 g of the product as a solid, m.p. 77°–79° C. This material was converted to the hydrochloride salt in 20 ml of warm ethanol by the addition of ethereal hydrogen chloride. The crystals which formed upon cooling and dilution with ether were collected and dried to give 3.1 g of white crystals, m.p. 210°–211° C.

ANALYSIS:

Calculated for $C_{16}H_{15}N_3 \cdot HCl$: 67.24%C 5.64%H 14.71%N Found: 67.15%C 5.67%H 14.76%N

EXAMPLE 6

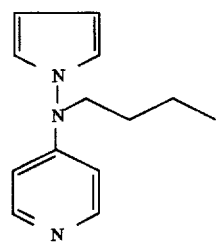

N-(Butyl)-N-(1H-pyrrol-1-yl)-4-pyridinamine hydrochloride

A solution of N-(1H-pyrrol-1-yl)-4-pyridinamine (4 g) in 20 ml of dimethylformamide was slowly added to an ice-cooled suspension of sodium hydride (60% oil dispersion, 1.1 g) in 5 ml of dimethylformamide. After the anion formation, a solution of 1-bromobutane (3.8 g) in 10 ml of dimethylformamide was slowly added. After thirty minutes, the reaction mixture was stirred with 300 ml of ice-water and extracted with ethyl acetate. The organic extract was washed with water and saturated sodium chloride solution, dried over anhydrous magnesium sulfate, filtered and evaporated to 5.5 g of an oil. This material was purified by HPLC (silica, ethyl acetate) to give 4.6 g of an oil. This oil was converted to the hydrochloride salt in 20 ml of warm isopropanol. The product which precipitated upon cooling was collected and dried to give 3.8 g of crystals, m.p. 178°–179° C.

ANALYSIS:

Calculated for $C_{13}H_{17}N_3 \cdot HCl$: 62.02%C 7.21%H 16.69%N Found: 62.03%C 7.27%H 16.61%N

EXAMPLE 7

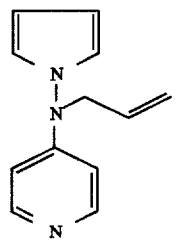

N-(2-Propenyl)-N-(1H-pyrrol-1-yl)-4-pyridinamine hydrochloride

To an ice-cooled suspension of sodium hydride (60% oil dispersion, 1.2 g, previously washed with hexanes) in 5 ml of dimethylformamide was slowly added a solution of N-(1H-pyrrol-1-yl)-4-pyridinamine (4 g) in 25 ml of dimethylformamide. After the anion formation, a solution of allyl bromide (3.1 g) in 5 ml of dimethylformamide was added. After stirring cold for one hour, the reaction mixture was stirred with water and extracted with ethyl acetate. The organic extract was washed with water and saturated sodium chloride solution, dried over anhydrous magnesium sulfate, filtered and evaporated to 6 g of an oil. This oil was purified by flash chromatography (silica, ethyl acetate) to give 5 g of an oil. This oil was converted to the hydrochloride salt and twice recrystallized from isopropanol/ether to give 3.5 g of crystals, m.p. 218°–219° C.

ANALYSIS:

Calculated for $C_{12}H_{13}N_3 \cdot HCl$: 61.14%C 5.99%H 17.83%N Found: 61.04%C 6.16%H 17.78%N

EXAMPLE 8

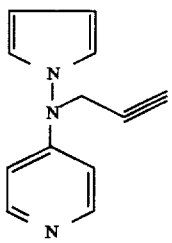

N-(2-Propynyl)-N-(1H-pyrrol-1-yl)-4-pyridinamine hydrochloride

To an ice-cold suspension of sodium hydride (60% oil dispersion, 3 g) in 10 ml of dimethylformamide was slowly added N-(1H-pyrrol-1-yl)-4-pyridinamine (10 g) in 70 ml of dimethylformamide. After the anion formation, a solution of propargyl bromide (80 wt. % in toluene, 11 g) in 10 ml of dimethylformamide was slowly added. After one hour, the reaction mixture was stirred with 500 ml of ice-water and extracted with ethyl acetate. The organic extract was washed with water and saturated sodium chloride solution, dried over anhydrous magnesium sulfate, filtered and evaporated to 20 g of oil. this oil was purified by HPLC (silica, ethyl acetate-dichloromethane) to give 12 g of oil. A four gram sample was converted to the hydrochloride salt in 30 ml of warm isopropanol to yield, upon cooling, 3.3 g of solid, m.p. 224°–225° C. (dec.). This material was recrystallized from isopropanol to give 2.7 g of solid, m.p. 230°–231° C. (dec.).

ANALYSIS:

Calculated for $C_{12}H_{11}N_3 \cdot HCl$: 61.67%C 5.18%H 17.98%N Found: 61.41%C 5.10%H 17.88%N

EXAMPLE 9

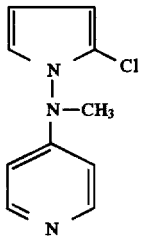

N-(2-Chloro-1H-pyrrol-1-yl)-N-methyl-4-pyridinamine hydrochloride

To a solution of N-methyl-N-(1H-pyrrol-1-yl)-4-pyridinamine (7.7 g) in 300 ml of anhydrous tetrahydrofuran cooled to 5° C. with an ice bath was added N-chlorosuccinimide (5.2 g). The reaction mixture was stirred sixty hours at ambient temperature, and thereafter additional N-chlorosuccinimide (0.9 g) was added. After stirring an additional sixteen hours at ambient temperature, the reaction mixture was stirred with an aqueous solution of sodium bisulfite and extracted with ether. The organic extract was washed with water and saturated sodium chloride solution and thereafter dried over anhydrous magnesium sulfate, filtered and evaporated to 9.5 g of an oil. This oil was purified by HPLC (silica, ethyl acetate) to give 4.4 g of an oil. This oil was purified by column chromatography (alumina, ether) to give 2.4 g of the desired product as an oil. This oil was dissolved in 25 ml of isopropanol, filtered, and converted to the hydrochloride salt by the addition of ethereal hydrochloric acid. The solution was diluted with 25 ml of ether and cooled. The resultant precipitate was collected and dried to give 2.5 g of crystals, m.p. 230°–231° C.

ANALYSIS:

Calculated for $C_{10}H_{10}ClN_3 \cdot HCl$: 49.20%C 4.54%H 17.22%N Found: 49.15%C 4.67%H 17.34%N

EXAMPLE 10

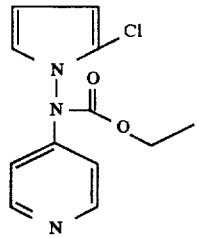

N-(2-Chloro-1H-pyrrol-1-yl)-N-(4-pyridinyl) carbamic acid ethyl ester hydrochloride To a solution of N-(4-pyridinyl)-N-(1H-pyrrol-1-yl) carbamic acid ethyl ester (9 g) in 100 ml of anhydrous tetrahydrofuran warmed to 50° C. was slowly dropped a solution of N-chlorosuccinimide (5.2 g) in 75 ml of anhydrous tetrahydrofuran. After stirring seven hours at 50° C., the reaction mixture was cooled, stirred with an aqueous solution of sodium bisulfite and extracted with ethyl acetate. The organic extract was washed with water and saturated sodium chloride solution and thereafter dried over anhydrous magnesium sulfate, filtered and evaporated to 11.5 g of an oil. This oil was purified by HPLC (silica, 20% ethyl acetate in dichloromethane) to give 3.8 g of the desired product as a solid. This material was converted to the hydrochloride salt and twice recrystallized from isopropanol-ether to give 3.3 g of crystals, m.p. 139°–140° C. (dec.).

ANALYSIS:

Calculated for $C_{12}H_{12}ClN_3O_2 \cdot HCl$: 47.70%C 4.34%H 13.91%N Found: 47.58%C 4.36%H 13.97%N

EXAMPLE 11

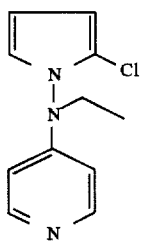

N-(2-Chloro-1H-pyrrol-1-yl)-N-ethyl-4-pyridinamine hydrochloride

To a solution of N-ethyl-N-(1H-pyrrol-1-yl)-4-pyridinamine (10.2 g) in 200 ml of anhydrous tetrahydrofuran was added N-chlorosuccinimide (7.3 g). After stirring twenty hours at ambient temperature, the reaction mixture was stirred with an aqueous solution of sodium sulfite and extracted with dichloromethane. The organic extract was washed with water and saturated sodium chloride solution and thereafter dried over anhydrous magnesium sulfate, filtered and evaporated to 12 g of an oil. This oil was purified by HPLC (silica, 25% dichloromethane in ethyl acetate) to give 3.7 g of the desired product as an oil. This oil was converted to the hydrochloride salt and twice recrystallized from isopropanol-ether to give 3.1 g of crystals, m.p. 206°–207° C.

ANALYSIS:

Calculated for $C_{11}H_{12}ClN_3 \cdot HCl$: 51.18%C 5.08%H 16.28%N Found: 51.43%C 4.95%H 16.36%N

EXAMPLE 12

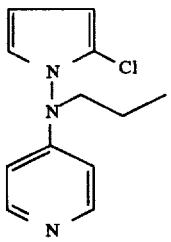

N-(2-Chloro-1H-pyrrol-1-yl)-N-proyl-4-pyridinamine hydrochloride

To a solution of N-propyl-N-(1H-pyrrol-1-yl)-4-pyridinamine (11 g) in 250 ml of tetrahydrofuran, cooled with an ice bath, was added N-chlorosuccinimide (8 g) as a powder. The reaction mixture was warmed to ambient temperature and after sixteen hours additional N-chlorosuccinimide (1 g) was added. After stirring for additional three hours, the reaction mixture was stirred with cold water, basified with sodium carbonate and extracted with ethyl acetate. The organic extract was washed with water and saturated sodium chloride solution, dried over anhydrous magnesium sulfate, filtered and evaporated to 14 g of oil. This oil was purified by HPLC (silica, ethyl acetate-dichloromethane) to give 4.1 g of pure product as an oil. This oil was converted to the hydrochloride salt and recrystallized twice from isopropanol-ether to give 2.4 g of crystals, m.p. 210°–211° C.

ANALYSIS:

Calculated for $C_{12}H_{14}ClN_3 \cdot HCl$: 52.95%C 5.56%H 15.44%N Found: 52.76%C 5.40%H 15.25%N

EXAMPLE 13

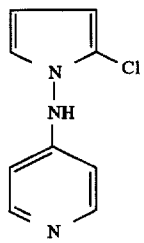

N-(2-Chloro-1H-pyrrol-1-yl)-4-pyridinamine hydrochloride

A mixture prepared from a solution of N-(2-chloro-1H-pyrrol-1-yl)-N-(4-pyridinyl)carbamic acid ethyl ester (6 g) in 50 ml of ethanol and 20 ml of 10% aqueous sodium hydroxide solution was warmed for 15 minutes on a steam bath, and thereafter cooled, diluted with 500 ml of water and extracted with dichloromethane. The organic extract was washed with water and saturated sodium chloride solution and thereafter dried over anhydrous magnesium sulfate, filtered and evaporated to 5 g of an oil. This oil was purified by HPLC (silica, ethyl acetate) to give 3.5 g of a solid, m.p. 115°–118° C. This material was converted to the hydrochloride salt and recrystallized twice from isopropanol-ether to give 3.4 g of crystals., m.p. 172°–173° C.

ANALYSIS:

Calculated for $C_9H_8ClN_3 \cdot HCl$: 46.98%C 3.94%H 18.27%N Found: 46.76%C 3.80%H 18.13%N

EXAMPLE 14

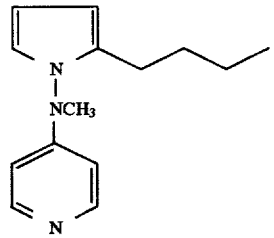

2-Butyl-N-methyl-N-(1H-pyrrol-1-yl)-4-pyridinamine maleate

To a solution of N-methyl-N-(1H-pyrrol-1-yl)-4-pyridinamine (4.2 g) in 50 ml of anhydrous tetrahydrofuran cooled to −78° C. under nitrogen, was slowly dropped n-butyllithium (2.1 molar in hexane, 13.8 ml). After the addition, the mixture was slowly warmed to ambient temperature. After stirring thirty minutes at ambient temperature, the reaction mixture was stirred with 300 ml of water and extracted with ethyl acetate. The organic extract was washed with water and saturated sodium chloride solution, dried over anhydrous magnesium sulfate, filtered and evaporated to 8.2 g of an oil. This oil was purified by HPLC (silica, 50% ethyl acetate-dichloromethane) to give 3.7 g of an oil. This oil was dissolved in 25 ml of warm isopropanol, and filtered, and a solution of maleic acid (1.9 g) in isopropanol was added. The crystals which formed upon cooling were collected and dried to give 5 g of crystals, m.p. 98°–110° C.

ANALYSIS:

Calculated for $C_{14}H_{19}N_3 \cdot C_4H_4O_4$: 62.59%C 6.71%H 12.17%N Found: 62.33%C 6.81%H 11.90%N

EXAMPLE 15

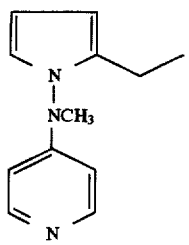

N-(2-Ethyl-1H-pyrrol-1-yl)-N-methyl-4-pyridinamine hydrochloride

A solution of N-(2-ethenyl-1H-pyrrol-1-yl)-N-methyl-4-pyridinamine (5.2 g) in 250 ml of ethanol containing 350 mg of platinum oxide was hydrogenated at 344.74 kilopascals (hereafter "KPa") [50 pounds per square inch (hereafter "psi")] for three hours and thereafter the product was filtered and evaporated to 5 g of oil. This oil was purified by flash chromatography (silica, 25% dichloromethane in ethyl acetate) to give 3.9 g of oil. This oil was converted to the hydrochloride salt and recrystallized twice from isopropanol-ether to give 3.0 g of crystals, m.p. 197°–198° C.

ANALYSIS:

Calculated for $C_{12}H_{15}N_3 \cdot HCl$: 60.62%C 6.78%N 17.68%N Found: 60.32%C 6.77%H 17.54%N

EXAMPLE 16

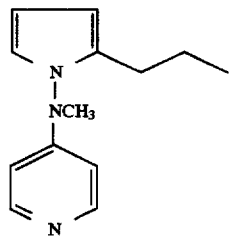

N-Methyl-N-(2-propyl-1H-pyrrol-1-yl)-4-pyridinamine hydrochloride

A solution of N-[2-(1-propenyl)-1H-pyrrol-1-yl)-N-methyl-4-pyridinamine (7 h) in 250 ml of ethanol containing 350 mg of platinum oxide was hydrogenated at 344.74 Kpa 50 psi) for two days, and thereafter the product was filtered and evaporated to 9 g of oil. This oil was purified by flash chromatography (silica, ethyl acetate) to give 8 g of oil. This oil was purified by column chromatography (alumina, ether) to give 5 g of oil. This oil was converted to the hydrochloride salt and recrystallized from isopropanol-ether and from ethanol-ether to give 2.8 g of crystals, m.p. 210°–212° C.

ANALYSIS:

Calculated for $C_{13}H_{17}N_3 \cdot HCl$: 62.02%C 7.21%H 16.69%N Found: 61.92%C 7.24%H 16.64%N

EXAMPLE 17

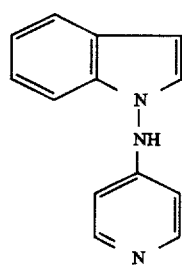

N-(4-Pyridinyl)-1H-indol-1-amine maleate

A solution of 1H-indol-1-amine (30 g), 4-chloropyridine hydrochloride (34 g) and pyridine (18 g) in 250 ml of isopropanol was stirred at 85° C. for 1.5 hours, and thereafter cooled, stirred with ice-water, basified with sodium carbonate and extracted with dichloromethane. The organic extract was washed with water and saturated sodium chloride solution, was dried over anhydrous magnesium sulfate, filtered and concentrated to a dark oil. This oil was purified by flash chromatography (silica, ethyl acetate) and thereafter by column chromatography (alumina, ether) to give 24 g of oil. A 3.6 g sample was purified by high performance liquid chromatography (silica, ethyl acetate) to give 3.5 g of oil. This oil was converted to the maleate salt and recrystallized twice from methanol/ether to give 3.8 g of needles, m.p. 145°–146° C. (dec.).

ANALYSIS:

Calculated for $C_{13}H_{11}N_3 \cdot C_4H_4O_4$: 62.75%C 4.65%N 12.92%N Found: 62.62%C 4.81%H 12.73%N

EXAMPLE 18

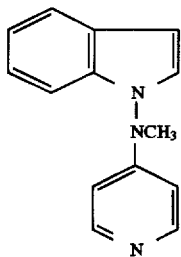

N-Methyl-N-(4-pyridinyl)-1H-indol-1-amine maleate

A solution of N-(4-pyridinyl)-1H-indol-1-amine (7.4 g) in 30 ml of dimethylformamide was added to an ice-cooled suspension of sodium hydride (1.6 g of 60% sodium hydride dispersion in mineral oil was washed with hexanes, the liquid portion was decanted and the residual solid was dispersed in 10 ml of dimethylformamide). After anion formation, a solution of dimethylsulfate (5 g) in 10 ml of dimethylformamide was added. After one hour of stirring at ambient temperature, the reaction mixture was stirred with ice-water and extracted with ether. The organic extract was washed with water and saturated sodium chloride solution, dried over anhydrous magnesium sulfate, filtered and concentrated to 8 g of oil. This oil was purified by flash chromatography (silica, ethyl acetate) and HPLC (silica, ethyl acetate) to give 2.9 g of oil. This oil was converted to the maleate salt and was recrystallized twice from methanol/ether to give 2.1 g of crystals, m.p. 103°–104° C.

21

ANALYSIS:

Calculated for $C_{14}H_{13}N_3 \cdot C_4H_4O_4$: 63.70%C 5.05%H 12.39%N Found: 63.36%C 4.93%H 12.39%N

EXAMPLE 19

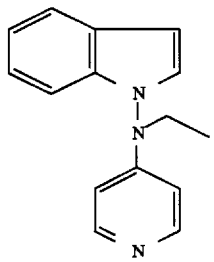

N-Ethyl-N-(4-pyridinyl)-1H-indol-1-amine maleate

To an ice-cooled suspension of sodium hydride (1.7 g of 60% sodium hydride dispersion in mineral oil was washed with hexanes, the liquid was decanted and the residual solid was dispersed in 5 ml of dimethylformamide) was slowly added a solution of N-(4-pyridinyl)-1H-indol-1-amine (7.6 g) in 25 ml of dimethylformamide. After anion formation, a solution of diethyl sulfate (6.4 g) in 10 ml of dimethylformamide was slowly added. After one hour, the mixture was stirred with ice-water and extracted with ethyl acetate. The organic extract was washed with water and saturated sodium chloride solution, was dried over anhydrous magnesium sulfate, filtered and concentrated to 11 g of oil. This oil was purified by flash chromatography (silica, ethyl acetate) to give 6.2 g of oil. This oil was purified by column chromatography (alumina, ether) to give 6 g of oil. A 3 g sample was convened to the maleate salt and recrystallized from ethanol/ether and thereafter from methanol/ether to give 2.7 g of crystals, m.p. 119°-120° C.

ANALYSIS:

Calculated for $C_{15}H_{15}N_3 \cdot C_4H_4O_4$: 64.58%C 5.42%H 11.89%N Found: 64.27%C 5.49%H 12.11%N

EXAMPLE 20

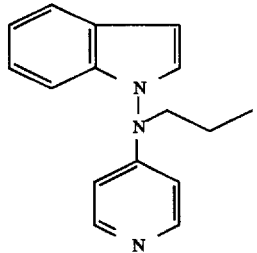

Part A: N-Propyl-N-(4-pyridinyl)-1H-indol-1-amine maleate

A solution of N-(4-pyridinyl)-1H-indol-1-amine (6 g) in 25 ml of dimethylformamide was slowly added to an ice-cooled suspension of sodium hydride (1.3 g of 60% sodium hydride dispersion in mineral oil was washed with hexanes, the liquid was decanted and the residual solid was dispersed in 5 ml of dimethylformamide). After anion formation, a solution of 1-bromopropane (4 g) in 5 ml of dimethylformamide was added. After one hour of stirring at ambient temperature, the reaction mixture was stirred with ice-water

22 and extracted with dichloromethane. The organic extract was washed with water and saturated sodium chloride solution, dried over anhydrous magnesium sulfate, filtered and concentrated to 8 g of oil. This oil was purified by HPLC (silica, ethyl acetate) and thereafter by column chromatography (alumina, ether) to give 6.4 g oil. This oil was converted to the maleate salt and recrystallized form methanol/ether to give 6.8 g of crystals, m.p. 115°-116° C.

ANALYSIS:

Calculated for $C_{16}H_{17}N_3 \cdot C_4H_4O_4$: 65.38%C 5.76%H 11.44%N Found: 65.26%C 5.71%H 11.34%N Part B: N-Propyl-N-(4-pyridinyl)-1H-indol-1-amine hydrochloride The free base oil was converted to the hydrochloride salt which was recrystallized from methanol; m.p. 212°-214° C.

ANALYSIS:

Calculated for $C_{16}H17N_3 \cdot HCl$: 66.78%C 6.03%H 14.60%N Found: 66.77%C 6.39%H 14.59%N

EXAMPLE 21

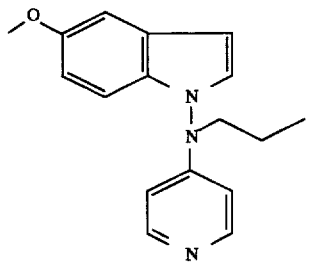

5-Methoxy-N-propyl-N-(4-pyridinyl)-1H-indol-1-amine maleate

To an ice-cooled suspension of sodium hydride (0.5 g of 60% sodium hydride dispersion in mineral oil was washed with hexanes, the liquid was decanted and the residual solid was dispersed in 5 ml of dimethylformamide) was slowly added a solution of 5-methoxy-N-(4-pyridinyl)-1H-indol-1-amine (2.3 g) in 20 ml of dimethylformamide. After anion formation, a solution of 1-bromopropane (1.4 g) in 5 ml of diemthylformamide was added. After one hour of stirring, the reaction mixture was stirred with ice-water and extracted with dicloromethane. The organic extract was washed with water and saturated sodium chloride solution, dried over anhydrous magnesium sulfate, filtered and concentrated to 2.3 g of oil. This oil was purified by flash chromatography (silica, ethyl acetate) to give 2.1 g of oil. This oil was converted to the maleate salt in ethanol/ether to give 2.0 g of crystals, m.p. 138°-139° C.

ANALYSIS:

Calculated for $C_{17}H_{19}N_3O \cdot C_4H_4O_4$: 63.46%C 5.83%H 10.58%N Found: 63.26%C 5.77%H 10.47%N

EXAMPLE 22

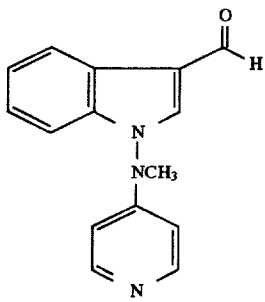

N-Methyl-N-(4-pyridinyl)-1H-indol-1-amine-3-carboxaldehyde maleate

To ice-cooled dimethylformamide (4 g) was slowly added phosphorous oxychloride (7 g). After complex formation, a solution of N-methyl-N-(4-pyridinyl)-1H-indol-1-amine (5 g) in 50 ml of dichloroethane was added. After one hour of stirring at 85° C., the reaction mixture was cooled, hydrolyzed with a solution of sodium acetate (5 g) in 25 ml of water, again cooled, basified with sodium carbonate and extracted with dichloromethane. The organic extract was washed with water and saturated sodium chloride solution, dried over anhydrous magnesium sulfate, filtered and concentrated to 6 g of oil. This oil was purified by flash chromatography (silica, ethyl acetate) to give 4.6 g of oil. This oil was converted to the maleate salt and recrystallized from ethanol/ether and thereafter from methanol/ether to give 2.6 g of crystals, m.p. 162°–163° C. (dec.).

ANALYSIS:

Calculated for $C_{15}H_{13}N_3O \cdot C_4H_4O_4$: 62.12%C 4.66%H 11.44%N Found: 61.71%C 4.62%H 11.14%N

EXAMPLE 23

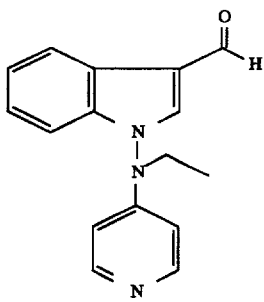

N-Ethyl-N-(4-pyridinyl)-1H-indol-1-amine-3-carboxaldehyde maleate

To ice-cooled dimethylformamide (2.2 g) was slowly added phosphorus oxychloride (4.5 g). After complex formation, a solution of N-ethyl-N-(4-pyridinyl)-1H-indol-1-amine (3.5 g) in 50 ml of dichloroethane was added. The mixture was stirred at 80° for one hour and thereafter hydrolyzed with a solution of sodium acetate (5 g) in 25 ml of water, cooled, basified with sodium carbonate and extracted with dichloromethane. The organic extract was washed with water and saturated sodium chloride solution, dried over anhydrous magnesium sulfate, filtered and concentrated to 5 g of oil. This oil was purified by flash chromatography (silica, ethyl acetate) to give 3.5 g of oil. This oil was converted to the maleate salt and recrystallized form ethanol/ether and thereafter from methanol/ether to give 3 g of solid, m.p. 170°–171° C. (dec.).

ANALYSIS:

Calculated for $C_{16}H_{15}N_3O \cdot C_4H_4O_4$: 62.98%C 5.02%H 11.02%N Found: 62.97%C 5.08%H 11.06%N

EXAMPLE 24

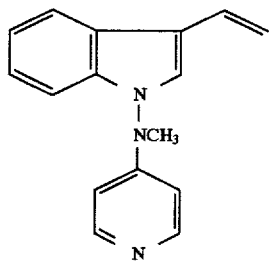

3-Ethenyl-N-methyl-N-(4-pyridinyl)-1H-indol-1-amine maleate

To an ice-cooled suspension of methyltriphenylphosphonium bromide (13 g) in 100 ml of anhydrous ether was added potassium tert-butoxide (4 g). After phosphorane formation, a solution of N-ethyl-N-(4-pyridinyl)-1H-indol-1-amine-3-carboxaldehyde (7.5 g) in 50 ml of ether and 50 ml of tetrahydrofuran was added. After one hour of stirring, the reaction mixture was stirred with water and extracted with ether. The organic extract was washed with water and saturated sodium chloride solution, dried over anhydrous magnesium sulfate, filtered and concentrated to 20 g of oil. This oil was purified by flash chromatography (silica, ethyl acetate) to give 7 g of oil. A 3.5 g sample was converted to the maleate salt in ethanol and recrystallized from methanol ether to give 3 g of crystals, m.p. 153°–154° C.

ANALYSIS:

Calculated for $C_{16}H_{15}N_3 \cdot C_4H_4O_4$: 65.74%C 5.24%H 11.50%N Found: 65.94%C 5.39%H 11.45%N

EXAMPLE 25

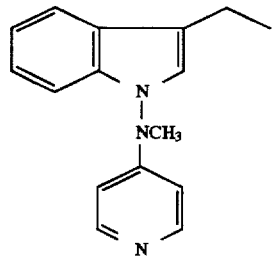

3-Ethyl-N-methyl-N-(4-pyridinyl)-1H-indol-1-amine hydrochloride

A solution of 3-ethenyl-N-methyl-N-(4-pyridinyl)-1H-indol-1-amine (5 g) in 250 ml of ethanol containing 0.5 g of platinum oxide was hydrogenated at 344.74 Kpa (50 psi) for one hour. The mixture was filtered and the filtrate was concentrated to 5 g of oil. This oil was purified by flash chromatography (silica, ethyl acetate) to give 3.5 g of oil. This oil was converted to the hydrochloride salt in ethanol/ether and recrystallized form methanol/ether to give 3.0 g of crystals, m.p. 262° C. (dec.).

ANALYSIS:

Calculated for $C_{16}H_{17}N_3 \cdot HCl$: 66.77%C 6.30%H 14.60%N Found: 66.87%C 6.33%H 14.57%N

EXAMPLE 26

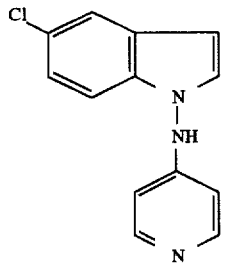

5-Chloro-N-(4-pyridinyl)-1H-indol-1-amine maleate

A solution of 5-chloro-1H-indol-1-amine (9 g), 4-chloropyridine hydrochloride (12 g) and pyridine (6.4 g) in 100 ml of isopropanol was stirred at reflux for one hour, cooled and stirred with ice-water, and the mixture was basified with sodium carbonate, extracted with dichloromethane and filtered. The organic extract was washed with water and saturated sodium chloride solution, dried over anhydrous magnesium sulfate, filtered and concentrated to a dark oil. This oil was purified by flash chromatography (silica, ethyl acetate) to give 6.2 g of oil. This oil was converted to the maleate salt in methanol-ether to give 7 g of crystals, m.p. 148°–150° C. A 2.6 g sample was recrystallized from methanol-ether to give 2.4 g of crystals, m.p. 150°–152° C.

ANALYSIS:

Calculated for $C_{13}H_{10}ClN_3 \cdot C_4H_4O_4$: 56.75%C 3.92%H 11.68%N Found: 56.71%C 4.00%H 11.62%N

EXAMPLE 27

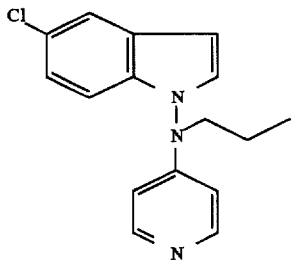

5-Chloro-N-propyl-N-(4-pyridinyl)-1H-indol-1-amine maleate

A solution of 5-chloro-N-(4-pyridinyl)-1H-indol-1-amine (3.3 g) in 15 ml of dimethylformamide was slowly added to an ice-cooled suspension of sodium hydride (0.65 g of 60% oil dispersion was washed with hexanes) in 5 ml of dimethylformamide. After anion formation a solution of 1-bromopropane (2 g) in 5 ml of dimethylformamide was added. After one hour the reaction mixture was stirred with ice-water and extracted with dichlormethane. The organic extract was washed with water and saturated sodium chloride solution, was dried over anhydrous magnesium sulfate, filtered and concentrated to 5 g of oil. This oil was purified by flash chromatography (silica, ethyl acetate) to give 3.1 g of oil. This oil was converted to the maleate salt in ethanol-ether and thereafter recrystallized from methanol-ether to give 3.4 g of crystals, m.p. 130° C.

ANALYSIS:

Calculated for $C_{16}H_{16}ClN_3 \cdot C_4H_4O_4$: 59.77%C 5.02%H 10.46%N Found: 59.97%C 5.13%H 10.35%N

EXAMPLE 28

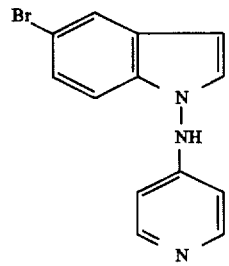

5-Bromo-N-(4-pyridinyl)-1H-indol-1-amine maleate

A solution of 5-bromo-1H-indol-1-amine (13 g), 4-chloropyridine hydrochloride (14 g) and pyridine (7.2 g) in 100 ml of isopropanol was stirred at reflux for one hour, cooled and stirred with ice-water, and thereafter the mixture was basified with sodium carbonate, extracted with dichloromethane and filtered. The organic extract was washed with water and saturated sodium chloride solution, dried over anhydrous magnesium sulfate, filtered and concentrated to a dark oil. This oil was purified by flash chromatography (silica, ethyl acetate) to give 11 g of oil. This oil was converted to the maleate salt in ethanol-ether to give 13 g of solid, m.p. 155°–157° C. dec. A three gram sample was recrystallized from methanol-ether to give 2.8 g of crystals, m.p. 161°–162° C. (dec.).

ANALYSIS:

Calculated for $C_{13}H_{10}BrN_3 \cdot C_4H_4O_4$: 50.51%C 3.49%H 10.40%N Found: 50.46%C 3.56%H 10.40%N

EXAMPLE 29

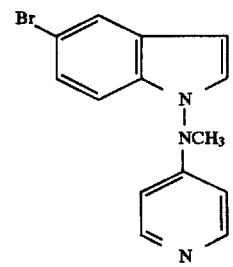

5-Bromo-N-methyl-N-(4-Pyridinyl)-1H-indol-1-amine maleate

A solution of 5-bromo-N-(4-pyridinyl)-1H-indol-1-amine (2.7 g) in 20 ml of dimethylformamide was slowly added to an ice-cooled suspension of sodium hydride (0.45 g of 60% oil dispersion was washed with hexanes) in 5 ml of dimethylformamide. After anion formation a solution of dimethylsulfate (1.4 g) in 5 ml of dimethylformamide was added. After one hour the reaction mixture was stirred with ice-water and extracted with dichloromethane. The organic extract was washed with water and saturated sodium chloride solution, dried over anhydrous magnesium sulfate, filtered and concentrated to 2 g of oil. This oil was purified by flash chromatography (silica, ethyl acetate) to give 1.4 g of oil. This oil was converted to the maleate salt in ethanol-ether to give 1.2 g of crystals, m.p. 110°–111° C.

ANALYSIS:

Calculated for $C_{14}H_{12}BrN_3 \cdot C_4H_4O_4$: 51.69%C 3.86%H 10.05%N Found: 51.55%C 3.89%H 10.14%N

EXAMPLE 30

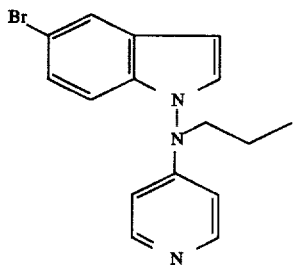

5-Bromo-N-propyl-N-(4-pyridinyl)-1H-indol-1-amine maleate

A solution of 5-bromo-N-(4-pyridinyl)-1H-indol-1-amine (4.9 g) in 25 ml of dimethylformamide was slowly added to an ice-cooled suspension of sodium hydride (0.8 g of 60% oil dispersion was washed with hexanes) in 5 ml of dimethylformamide. After anion formation a solution of 1-bromopropane (2.5 g) in 5 ml of dimethylformamide was added. After one hour the reaction mixture was stirred with ice-water and extracted with dichloromethane. The organic extract was washed with water and saturated sodium chloride solution, dried over anhydrous magnesium sulfate, filtered and concentrated to 5 g of oil. This oil was purified by flash chromatography (silica, ethyl acetate) to give 4.5 g of oil. This oil was converted to the maleate salt in ethanol-ether to give 5.4 g of solid, m.p. 150°–152° (dec.). This solid was recrystallized from methanol-ether to give 4.8 g of crystals, m.p. 157°–158° C. (dec.).

ANALYSIS:

Calculated for $C_{16}H_{16}BrN_3 \cdot C_4H_4O_4$: 53.82%C 4.52%H 9.42%N Found: 53.63%C 4.62%H 9.40%N

EXAMPLE 31

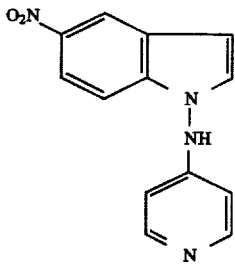

5-Nitro-N-(4-pyridinyl)-1H-indol-1-amine hydrochloride

A solution of 5-nitro-1H-indol-1-amine (4.5 g) and 4-chloropyridine hydrochloride (4.5 g) in 175 ml of isopropanol was stirred at reflux for two hours, another equivalent of 4-chloropyridine hydrochloride was added and the mixture was refluxed for two additional hours. The reaction mixture was then cooled, stirred with water, basified with sodium carbonate and extracted with ethyl acetate. The organic extract was washed with water and saturated sodium chloride solution, dried over anhydrous magnesium sulfate, filtered and concentrated to 9 g of dark oil. This oil was purified by flash chromatography (silica, ethyl acetate) to give 3.8 g of light brown solid, m.p. 183°–184° C. This material was converted to the hydrochloride salt and recrystallized twice from methanol/ether to give 3.5 g of orange needles, m.p. 300°–302° C. (dec.).

ANALYSIS:

Calculated for $C_{13}H_{10}N_4O_2 \cdot HCl$: 53.71%C 3.81%H 19.28%N Found: 53.55%C 3.77%H 19.17%N

EXAMPLE 32

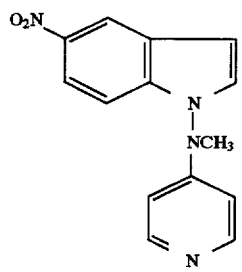

N-Methyl-5-nitro-N-(4-pyridinyl)-1H-indol-1-amine maleate

A solution of 5-nitro-N-(4-pyridinyl)-1H-indol-1-amine (6 g) in 20 ml of dimethylformamide was slowly added to an ice-cooled sodium hydride suspension prepared by washing 1.2 g of 60% sodium hydride suspension in oil with hexanes and suspending the residue in 5 ml of dimethylformamide. After the anion formation a solution of dimethyl sulfate (3.7 g) in 10 ml of dimethylformamide was added. After one hour the reaction mixture was stirred with water and extracted with ethyl acetate. The organic extract was washed with water and saturated sodium chloride solution, dried over anhydrous magnesium sulfate, filtered and concentrated to 6 g of dark oil. This was purified by flash chromatography (silica, ethyl acetate) to give 2.7 g of orange solid, m.p. 149°–150° C. This was converted to the maleate salt and recrystallized twice from methanol/ether to give 2.7 g of orange crystals, m.p. 174°–175° C. (dec.).

ANALYSIS:

Calculated for $C_{14}H_{12}N_4O_2 \cdot C_4H_4O_4$: 56.25%C 4.20%H 14.58%N Found: 56.14%C 4.27%H 14.46%N

EXAMPLE 33

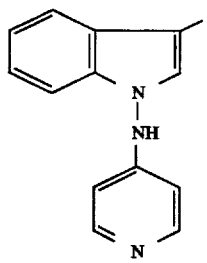

3-Methyl-N-(4-pyridinyl)-1H-indol-1-amine oxalate

To 200 ml of isopropanol were added 4-chloropyridine hydrochloride (7.5 g) and 3-methyl-1H-indol-1-amine (7.6 g). The mixture was stirred at 90° C. for six hours, and thereafter poured into 400 ml of ice water, and stirred for five minutes. The pH was adjusted to 10 with sodium carbonate solution and then extracted with ethyl acetate. The organic layer was washed with water and brine, dried over anhydrous magnesium sulfate, filtered and evaporated to obtain 8.4 g of thick brown oil, which was eluted on a silica gel column with ethyl acetate via HPLC. The desired fractions were combined and concentrated to 7.4 g of brown oil. A 2.3 g sample of this oil was dissolved in 50 ml of ethanol, and the pH adjusted to 1 with an ethanolic solution of oxalic acid, and the solution was diluted with ether. The resultant white precipitate was collected and dried to give 4.0 g, m.p. 130°–135° C. (dec.). This material was recrystallized from ethanol/ether (1:1) to give 3.8 g, m.p. 137° C. (dec.).

ANALYSIS:

Calculated for $C_{14}H_{13}N_3 \cdot C_2H_2O_4$: 61.33%C 4.83%H 13.41%N Found: 61.41%C 4.96%H 13.28%N

EXAMPLE 34

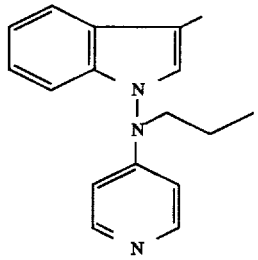

3-Methyl-N-propyl-N-(4-pyridinyl)-1H-indol-1-amine maleate

To a cold sodium hydride suspension prepared by washing 0.8 g of 60% sodium hydride suspension in oil with hexanes and suspending the residue in 15 ml of dry dimethylformamide was added a solution of 3-methyl-N-(4-pyridinyl)-1H-indol-1-amine (4.0 g) in 25 ml of dry dimethylformamide in ten minutes. After ten minutes a solution of propyl bromide (2.7 g) in 15 ml dimethylformamide was added. The mixture was stirred at ambient temperature for thirty minutes, poured into 200 ml of ice water, stirred for five minutes, and then extracted with ethyl acetate. The organic layer was washed with water and brine, dried over anhydrous magnesium sulfate, filtered and evaporated to give 5 g of brown oil, which was eluted on a silica gel column with ethyl acetate via HPLC. The desired fractions were combined and concentrated to 2.6 g of brown oil. This oil was dissolved in ether, the pH was adjusted to 1 with ethereal maleic acid, and the resultant white precipitate collected and dried to give, 4.0 g m.p. 148° C. (dec.). This material was recrystallized from methanol/ether (1:10) to give 3.5 g of white crystals, m.p. 148°–149° C.

ANALYSIS:

Calculated for $C_{17}H_{19}N_3 \cdot C_4H_4O_4$: 66.13%C 6.08%H 11.02%N Found: 66.15%C 6.02%H 11.00%N

EXAMPLE 35

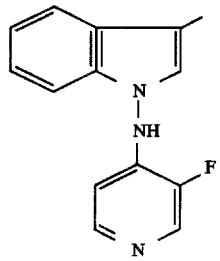

N-(3-Fluoro-4-pyridinyl)-3-methyl-1H-indol-1-amine

To 200 ml of isopropanol were added 4-chloro-3-fluoropyridine hydrochloride (10 g) and 3-methyl-1H-indol-amine (5.9 g). The mixture was stirred at 90° C. for four hours, cooled, and poured into 500 ml of ice water. The pH was adjusted to 10 with sodium carbonate solution, and the mixture was extracted with ethyl acetate. The organic layer was washed with water and brine, dried over anhydrous magnesium sulfate, filtered, and evaporated to give about 10 g of dark oil, which was eluted on a silica gel column first with dichloromethane, and then with ether/petroleum ether (1:1) via flash chromatography. The desired fractions were combined and concentrated to a yellow solid, 6.2 g, m.p. 450C. A sample of this material was recrystallized from isopropyl ether/hexanes (1:1) to give a yellow solid, m.p. 141°–142° C.

ANALYSIS:

Calculated for $C_{14}H_{12}FN_3$: 69.69%C 5.02%C 17.42%N Found: 69.52%C 5.01%H 17.57%N

EXAMPLE 36

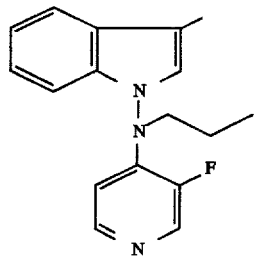

N-(3-Fluoro-4-pyridinyl)-N-propyl-3-methyl-1H-indol-1-amine hydrochloride

To a sodium hydride suspension prepared by washing 0.5 g of 60% sodium hydride suspension in oil with hexanes and suspending the residue in 10 ml of dimethylformamide, was added a solution of N-(3-fluoro-4-pyridinyl)-3-methyl-1H-indol-1-amine (3.0 g) in 20 ml of dimethylformamide at ice-bath temperature over ten minutes. The mixture was stirred for an additional five minutes, and thereafter a solution of propyl bromide (1.2 ml) in 10 ml of dimethylformamide was added in five minutes. The mixture was stirred at ambient temperature for thirty minutes, poured into 10 ml of ice-water, and then extracted with ethyl acetate. The organic layer was collected, washed with water and brine, dried over anhydrous magnesium sulfate, filtered, and evaporated to give 4 g of brown oil, which was eluted on a silica gel column with 20% ethyl acetate/dichloromethane via HPLC. The desired fractions were combined and concentrated to a thick yellow oil, 3.4 g. The oil was dissolved in ether, the pH adjusted to 1 with ethereal hydrogen chloride, and the resultant white precipitate collected and dried to give 3.4 g. This material was recrystallized from ethanol/ether (1:20) to give 2.7 g of white crystals, m.p. 193° C. (dec.).

ANALYSIS:

Calculated for $C_{17}H_{18}FN_3 \cdot HCl$: 63.84%C 5.99%H 13.14%N Found: 64.11%C 6.01%H 13.20%N

EXAMPLE 37

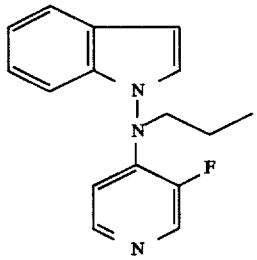

N-(3-Fluoro-4-pyridinyl)-N-propyl-1H-indol-1-amine hydrochloride

To a sodium hydride suspension prepared by washing 0.6 g of 60% sodium hydride suspension in oil with hexanes and suspending the residue in 10 ml of cold dimethylformamide, was added a solution of N-(3-fluoro-4-pyridinyl)-1H-indol-1-amine in 25 ml of dimethylformamide. The mixture was stirred at 5° C. for ten minutes, and thereafter a solution of bromopropane (1.4 ml) in 10 ml of dimethylformamide was added. The mixture was stirred at ambient temperature for thirty minutes, poured into 200 ml of ice water, stirred for five minutes, and extracted with ethyl acetate. The organic layer was washed with water and brine, dried over anhydrous magnesium sulfate, filtered and evaporated to give 3.2 g of brown oil, which was eluted on a silica gel column with 10% ethyl acetate/dichloromethane via HPLC. The desired fractions were combined and concentrated to 2.4 g of brown oil, which was dissolved in 40 ml of absolute ethanol. The pH was adjusted to 1 with ethereal hydrogen chloride and the solution was diluted with 400 ml of ether. The resultant off-white precipitate was collected and dried to give 2.1 g, m.p. 198°–200° C. (dec.).

ANALYSIS:

Calculated for $C_{16}H_{16}FN_3 \cdot HCl$: 62.85%C 5.60%H 13.74%N Found: 62.80%C 5.60%H 13.66%N

EXAMPLE 38

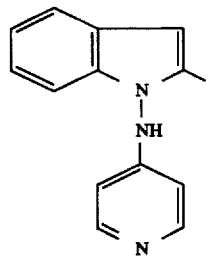

2-Methyl-N-(4-pyridinyl)-1H-indol-1-amine

The title compound was prepared from 2-methyl-1H-indol-1-amine and 4-chloropyridine hydrochloride at 120° C. for 30 minutes in substantially the same manner as in Example 17, m.p. 75°–78° C.

ANALYSIS:

Calculated for $C_{14}H_{13}N_3$: 75.31%C 5.87%H 18.82%N Found: 75.02%C 5.88%H 18.66%N

EXAMPLE 39

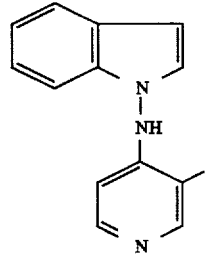

N-(3-Methyl-4-pyridinyl)-1H-indol-1-amine

The title compound was prepared from 1H-indol-1-amine and 4-chloro-3-methylpyridine hydrochloride in isopropanol at 90° C. for 6 hours in substantially the same manner as in Example 17, m.p. 78°–80° C.

ANALYSIS:

Calculated for $C_{14}H_{13}N_3$: 75.31%C 5.87%H 18.82%N Found: 74.98%C 5.83%H 18.86%N

EXAMPLE 40

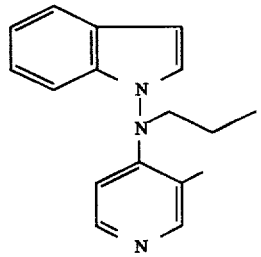

N-(3-Methyl-4-pyridinyl)-N-propyl-1H-indol-1-amine oxalate

The title compound was prepared from N-propyl-1H-indol-1-amine and 4-chloro-3-methylpyridine hydrochloride in 1-methyl-2-pyrrolidinone at 120° C. for 20 hours in substantially the same manner as in Example 17, m.p. 155° C. (dec.).

ANALYSIS:

Calculated for $C_{17}H_{19}N_3 \cdot C_2H_2O_4$: 64.21%C 5.96%H 11.82%N Found: 64.15%C 5.85%H 11.69%N

EXAMPLE 41

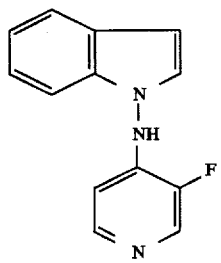

N-(3-Fluoro-4-pyridinyl)-1H-indol-1-amine hydrochloride

The title compound was prepared from 1H-indol-1-amine and 4-chloro-3-fluoropyridine hydrochloride in isopropanol at 90° C. for 4 hours in substantially the same manner as in Example 17, m.p. >250° C.

ANALYSIS:

Calculated for $C_{13}H_{10}FN_3 \cdot HCl$: 59.21%C 4.21%H 15.93%N Found: 59.35%C 4.36%H 15.81%N

EXAMPLE 42

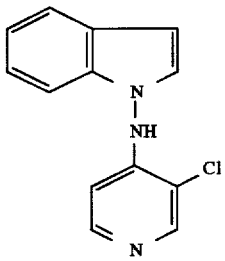

N-(3-Chloro-4-pyridinyl)-1H-indol-1-amine hydrochloride

The title compound was prepared from 1H-indol-1-amine and 3,4-dichloropyridine hydrochloride in isopropanol at 100° C. for 4 hours in substantially the same manner as in Example 17, m.p. >230° C.

ANALYSIS:

Calculated for $C_{13}H_{10}ClN_3 \cdot HCl$: 55.73%C 3.96%H 15.00%N Found: 55.97%C 4.23%H 14.64%N

EXAMPLE 43

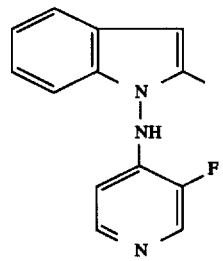

N-(3-Fluoro-4-pyridinyl)-2-methyl-1H-indol-1-amine

The title compound was prepared from 2-methyl-1H-indol-1-amine and 4-chloro-3-fluoropyridine hydrochloride in 1-methyl-2-pyrrolidone for 1 hour in substantially the same manner as in Example 17, m.p. 157°–158° C.

ANALYSIS:

Calculated for $C_{14}H_{12}FN_3$: 69.69%C 5.02%H 17.42%N Found: 69.53%C 4.95%H 17.28%N

EXAMPLE 44

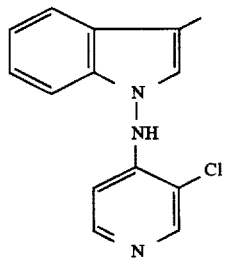

N-(3-Chloro-4-pyridinyl)-3-methyl-1H-indol-1-amine hydrochloride

The title compound was prepared from 3-methyl-1H-indol-1-amine and 3,4-dichloropyridine hydrochloride in isopropanol at 80° C. for 5 hours in substantially the same manner as in Example 17. Recrystallized from ethanol, m.p. 278°–280° C. (dec.).

ANALYSIS:

Calculated for $C_{14}H_{12}ClN_3 \cdot HCl$: 57.16%C 4.45%H 14.29%N Found: 57.20%C 4.44%H 14.28%N

EXAMPLE 45

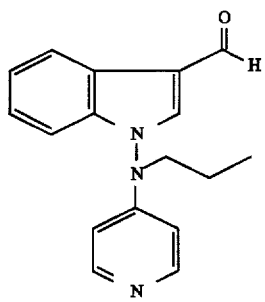

N-proyl-N-(4-pyridinyl)-1H-indol-1-amine-3-carboxaldehyde maleate

The title compound was prepared from N-propyl-N-(4-pyridinyl)-1H-indol-1-amine, phosphorous oxychloride and dimethylformamide in substantially the same manner as in Example 22, m.p. 169°–171° C.

ANALYSIS:

Calculated for $C_{17}H_{17}N_3O \cdot C_4H_4O_4$: 63.79%C 5.35%H 10.63%N Found: 63.67%C 5.38%H 10.58%N

EXAMPLE 46

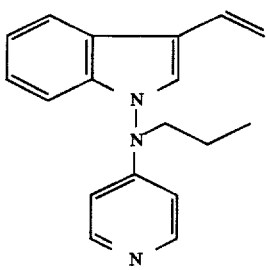

N-Propyl-N-(4-pyridinyl)-3-ethenyl-1H-indol-1-amine maleate

The title compound was prepared from N-propyl-N-(4-pyridinyl)-1H-indol-1-amine-3-carboxaldehyde, methyltriphenylphosphonium bromide and potassium-t-butoxide in substantially the same manner as in Example 24. Recrystallized from methanol/ether, m.p. 157°–158° C. (dec.).

ANALYSIS:

Calculated for $C_{18}H_{19}N_3 \cdot C_4H_4O_4$:67.16%C 5.89%H 10.68%N Found: 66.73%C 6.40%H 10.56%N

EXAMPLE 47

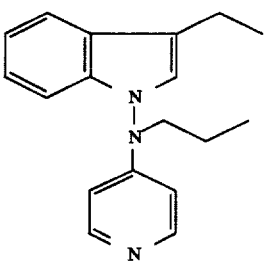

3-Ethyl-N-propyl-N-(4-pyridinyl)-1H-indol-1-amine maleate

The title compound was prepared by hydrogenating 3-ethenyl-N-propyl-N-(4-pyridinyl)-1H-indol-1-amine in substantially the same manner as in Example 25, m.p. 133°–134° C.

ANALYSIS:

Calculated for $C_{18}H_{21}N_3 \cdot C_4H_4O_4$:66.82%C 6.37%H 10.63%N Found: 66.73%C 6.40%H 10.62%N

EXAMPLE 48

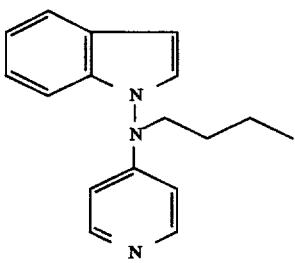

N-Butyl-N-(4-pyridinyl)-1H-indol-1-amine maleate

The title compound was prepared from N-(4-pyridinyl)-1H-indol-1-amine and 1-bromobutane with the aid of sodium hydride in substantially the same manner as in Example 20. Recrystallized from ethanol/ether (1:10), m.p. 108°–110° C.

ANALYSIS:

Calculated for $C_{17}H_{19}N_3 \cdot C_4H_4O_4$:66.13%C 6.08%H 11.02%N Found: 66.10%C 6.05%H 11.04%N

EXAMPLE 49

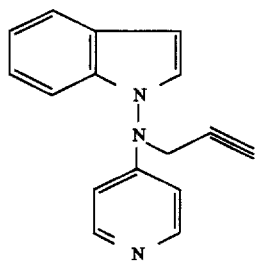

N-(2-Propynyl)-N-(4-pyridinyl)-1H-indol-1-amine maleate

The title compound was prepared from N-(4-pyridinyl)-1H-indol-1-amine and propargyl bromide with the aid of sodium hydride in substantially the same manner as in Example 20. Recrystallized from ethanol/ether, m.p. 107°–109° C.

ANALYSIS:

Calculated for $C_{16}H_{13}N_3 \cdot C_4H_4O_4$:66.11%C 4.72%H 11.56%N Found: 66.04%C 4.69%H 11.45%N

EXAMPLE 50

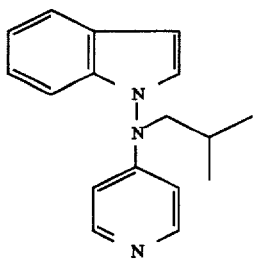

N-(2-Methylpropyl)-N-(4-pyridinyl)-1H-indol-1-amine maleate

The title compound was prepared from N-(4-pyridinyl)-1H-indol-1-amine and 1-bromo-2-methylpropane with the aid of sodium hydride in substantially the same manner as in Example 20, m.p. 101°–103° C.

ANALYSIS:

Calculated for $C_{17}H_{19}N_3 \cdot C_4H_4O_4$:66.13%C 6.08%H 11.02%N Found: 66.03%C 6.09%H 11.01%N

EXAMPLE 51

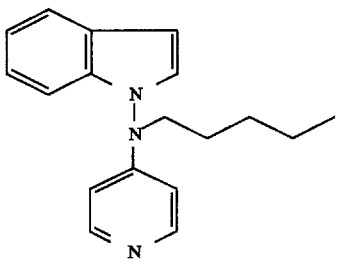

N-Pentyl-N-(4-pyridinyl)-1H-indol-1-amine maleate

The title compound was prepared from N-(4-pyridinyl)-1H-indol-1-amine and 1-bromopentane with the aid of sodium hydride in substantially the same manner as in Example 20. Recrystallized from ethanol/ether (1:9), m.p. 91°–93° C.

ANALYSIS:

Calculated for $C18H_{21}N3 \cdot C_4H_4O_4$: 66.82%C 6.37%H 10.63%N Found: 66.70%C 6.29%H 10.55%N

EXAMPLE 52

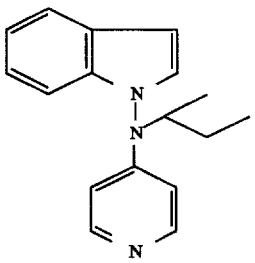

(N-(1-Methylpropyl)-N-(4-pyridinyl)-1H-indol-1-amine maleate

The title compound was prepared from N-(4-pyridinyl)-1H-indol-1-amine and 2-bromobutane with the aid of sodium hydride in substantially the same manner as in Example 20. Recrystallized from ethanol/ether, m.p. 117°–118° C.

ANALYSIS:

Calculated for $C_{17}H_{19}N_3 \cdot C_4H_4O_4$: 66.13%C 6.08%H 11.02%N Found: 65.78%C 5.97%H 10.98%N

EXAMPLE 53

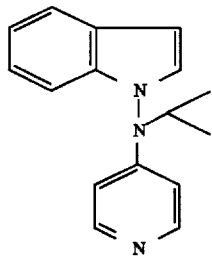

N-(1-Methylethyl)-N-(4-pyridinyl)-1H-indol-1-amine maleate

The title compound was prepared from N-(4-pyridinyl)-1H-indol-1-amine and 2-bromopropane with the aid of sodium hydride in substantially the same manner as in Example 20. Recrystallized from methanol/ether, m.p. 121°–123° C.

ANALYSIS:

Calculated for $C_{16}H_{17}N_3 \cdot C_4H_4O_4$: 65.38%C 5.76%H 11.44%N Found: 65.28%C 5.81%H 11.36%N

EXAMPLE 54

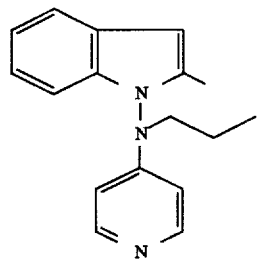

2-Methyl-N-propyl-N-(4-pyridinyl)-1H-indol-1-amine maleate

The title compound was prepared from 2-methyl-N-(4-pyridinyl)-1H-indol-1-amine and 1-bromopropane with the aid of sodium hydride in substantially the same manner as in Example 20, m.p. 155°–156° C. (dec.).

ANALYSIS:

Calculated for $C_{17}H_{19}N_3 \cdot C_4H_4O_4$: 66.13%C 6.08%H 11.02%N Found: 65.78%C 6.08%H 10.82%N

EXAMPLE 55

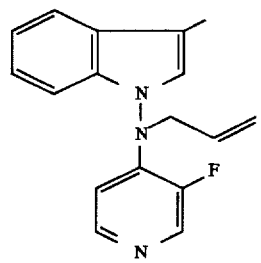

N-(3-Fluoro-4-pyridinyl)-N-(2-propenyl)-3-methyl-1H-indol-1-amine hydrochloride

The title compound was prepared from N-(3-fluoro-4-pyridinyl)-3-methyl-1H-indol-1-amine and allyl bromide with the aid of sodium hydride in substantially the same manner as in Example 20, m.p. 185°–187° C.

ANALYSIS:

Calculated for $C_{17}H_{16}FN_3 \cdot HCl$: 64.25%C 5.39%H 13.22%N Found: 64.15%C 5.39%H 13.08%N

EXAMPLE 56

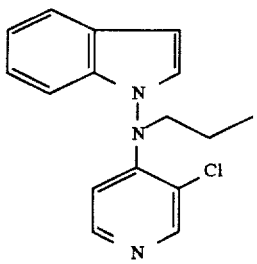

N-(3-Chloro-4-pyridinyl)-N-propyl-1H-indol-1-amine hydrochloride

The title compound was prepared from N-(3-chloro-4-pyridinyl)-1H-indol-1-amine and propyl bromide with the aid of sodium hydride in substantially the same manner as in Example 20, m.p. 202° C. (dec.).

ANALYSIS:

$C_{16}H_{16}ClN_3 \cdot HCl$: 59.63%C 5.32%H 13.04%N Found: 60.01%C 5.31%H 12.94%N

EXAMPLE 57

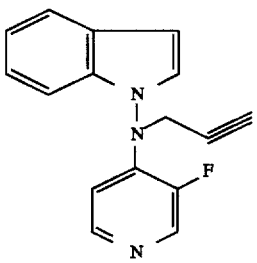

N-(3-Fluoro-4-pyridinyl)-N-(2-propynyl)-1H-indol-1-amine hydrochloride

The title compound was prepared from N-(3-fluoro-4-pyridinyl)-1H-indol-1-amine and propargyl bromide with the aid of sodium hydride in substantially the same manner as in Example 20. Recrystallized from methanol/ether (1:5), m.p. 211°–212° C.

ANALYSIS:

Calculated form $C_{16}H_{12}FN_3 \cdot HCl$: 63.68%C 4.34%H 13.93%N Found: 63.46%C 4.20%H 13.72%N

EXAMPLE 58

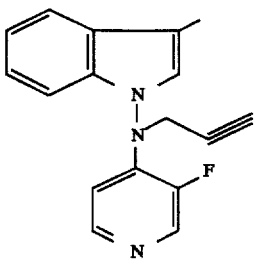

N-(3-Fluoro-4-pyridinyl)-3-methyl-N-(2-prolynyl)-1H-indol-1-amine hydrochloride

The title compound was prepared from N-(3-fluoro-4-pyridinyl)-3-methyl-1H-indol-1-amine and propargyl bromide with the aid of sodium hydride in substantially the same manner as in Example 20. Recrystallized from methanol/ether (1:5), m.p. 206°–207° C.

ANALYSIS:

Calculated for $C_{17}H_{14}FN_3 \cdot HCl$: 64.66%C 4.79%H 13.30%N Found: 64.49%C 4.70%H 13.18%N

EXAMPLE 59

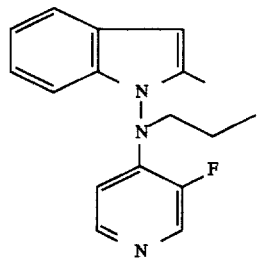

N-(3-Fluoro-4-pyridinyl)-2-methyl-N-propyl-1H-indol-1-amine

The title compound was prepared from N-(3-fluoro-4-pyridinyl)-2-methyl-1H-indol-1-amine and 1-bromopropane with the aid of sodium hydride in substantially the same manner as in Example 20, m.p. 5° C.

ANALYSIS:

Calculated for $C_{17}H_{11}FN_3$: 72.06%C 6.40%H 14.83%N Found: 71.76%C 6.51%H 14.48%N

EXAMPLE 60

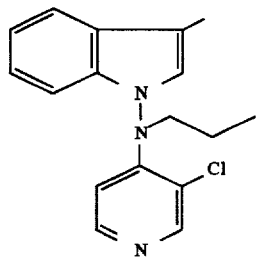

N-(3-Chloro-4-pyridinyl)-3-methyl-N-propl-1H-indol-1-amine

The title compound was prepared from N-(3-chloro-4-pyridinyl)-3-methyl-1H-indol-1-amine and 1-bromopropane with the aid of sodium hydride in substantially the same manner as in Example 20, m.p. 68°–70° C.

ANALYSIS:

Calculated for $C_{17}H_{18}ClN_3$: 68.10%C 6.05%H 14.02%N Found: 67.99%C 6.01%H 14.01%N

EXAMPLE 61

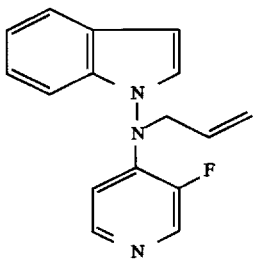

N-(3-Fluoro-4-pyridinyl)-N-(2propenyl)-1H-indol-1-amine hydrochloride

To a cold solution of N-(3-fluoro-4-pyridinyl)-1H-indol-1-amine (2.9 g) in 70 ml of dry tetrahydrofuran was added potassium tert-butoxide (1.7 g), and the mixture was stirred at 0° C. for two minutes. To this was added a solution of allyl bromide (1.3 ml) in 10 ml of tetrahydrofuran. After stirring at 0° C. for 2 hours, the mixture was poured into 100 ml water, stirred for 5 minutes and extracted with ethyl acetate (3x). The organic layer was washed with water and brine, dried over anhydrous magnesium sulfate, filtered, and concentrated to an oil (3.0 g) which was eluted on a silica gel column with 50% ethyl acetate/dichloromethane via HPLC. The desired fractions were combined and concentrated to an oil (2.0 g) which was dissolved in ethanol. The pH was adjusted to 1 with ethereal hydrogen chloride and the solution was diluted with ether. The resultant precipitate was collected and dried to give 2.0 g of the title compound, m.p. 204°–205° C.

ANALYSIS:

Calculated for $C_{16}H_{14}FN_3 \cdot HCl$: 63.26%C 4.98%H 13.83%N Found: 63.25%C 4.98%H 13.70%N

EXAMPLE 62

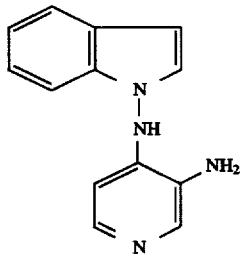

4-[N-(1H-indol-1-yl)]-3,4-pyridinamine hemihydrate

To a slurry of 10% palladium on carbon (1.0 g) in 5 ml absolute ethanol was added N-(1H-indol-1-yl)-3-nitro-4-pyridinamine (5.0 g) in 245 ml of absolute ethanol. The mixture was hydrogenated (Parr apparatus)at 344.74 Kpa (50 psi) for two hours. The mixture was filtered and the filtrate evaporated to yield a brown oil (5.4g) which was eluted with 5% methanol/dichloromethane on a silica gel column via HPLC. The fractions containing product were evaporated to yield a solid (3.8g) which was eluted with 5% methanol/dichloromethane on silica gel column via HPLC. The desired fractions were evaporated to yield 2.5 g of the title compound as a solid, m.p. 74°–80° C.

ANALYSIS:

Calculated for $C_{13}H_{12}N_4 \cdot O_5H_2O$: 66.93%C 5.62%H 24.04%N Found: 67.31%C 5.22%H 23.98%N

EXAMPLE 63

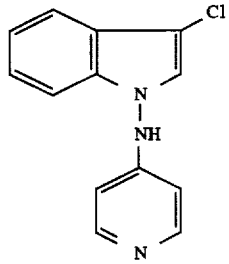

3-Chloro-N-(4-pyridinyl)-1H-indol-1-amine salicylate

A suspension of crude 3-chloro-1H-indol-1-amine (65.5 g) and 4-chloropyridine hydrochloride (45 g) in 1-methyl-2-pyrrolidinone (250 ml) was stirred at 60° C. for eight hours. The cooled reaction mixture was quenched into 5% aqueous sodium hydroxide, extracted into toluene, dried and concentrated to give an oil. A portion of this oil was dissolved in ethyl acetate. Salicylic acid (1.2 eq) was added to precipitate the salt. The solid was collected at room temperature and dried. This solid was recrystallized with a charcoal treatment from methanol and oven dried (75° C., house vacuum) overnight to yield 10.9 g of the title compound as a solid, m.p. 185°–186° C. (dec.).

ANALYSIS:

Calculated for $C_{20}H_{16}N_3O_3Cl$: 62.91%C 4.22%H 11.01%N Found: 62.74%C 4.12%H 10.93%N

EXAMPLE 64

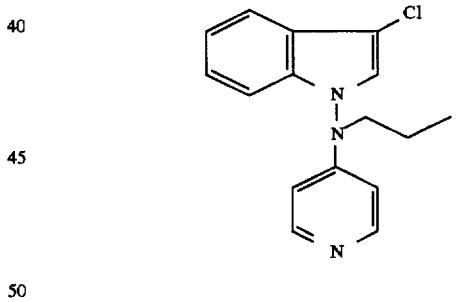

3-Chloro-N-propyl-N-(4-pyridinyl)-1H-1-amine hydrochloride

To a cold (−10° C.) solution of 3-chloro-N-4-pyridinyl-1H-indol-1-amine (4.5 g) in dry dimethylformamide (36 ml) was added potassium tert-butoxide (2.3 g) portionwise to maintain a temperature of approximately −10° C. After ageing at 0° C. for one hour, a solution of 1-bromopropane (2.2 ml) in dry dimethylformamide (8.8 ml) was added, maintaining a temperature of approximately 0° C. After stirring at 0° C. for three hours, the reaction mixture was quenched with water, extracted into ethyl acetate, dried and concentrated to give a dark oil. A portion of this oil was purified by flash chromatography on silica gel using 9:1 dichloromethane/methanol as the eluting solvent. The fractions which contained product were combined, treated with charcoal and concentrated to give an oil. A portion of this oil was dissolved in ether and ethereal hydrogen chloride was added to precipitate the salt. This salt was isolated at room temperature and suction dried. The solid was dissolved in methanol and methyl-tert-butyl ether was added to precipitate the product. The solid was isolated at room temperature and dried (70° C.) under house vacuum to yield 3.7 g of the title compound as a solid, m.p. 257°–260° C. (dec.).

ANALYSIS:

Calculated for $C_{16}H_{17}N_3C_{12}$: 59.64%C 5.32%H 13.04%N Found: 59.71%C 5.35%H 12.93%N

EXAMPLE 65

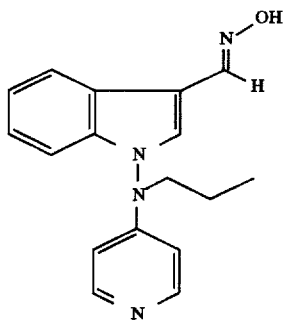

N-(n-Propyl)-N-(4-pyridinyl)-1H-indol-1-amine-3-carboxaldehyde oxime maleate

To a solution of N-(n-propyl)-N-(4-pyridinyl)-1H-indol-1-amine-3-carboxaldehyde (10 g) in 100 ml pyridine was added hydroxylamine hydrochloride (5 g). After stirring one hour at ambient temperature the reaction mixture was evaporated and the residue was stirred with water, basified with sodium carbonate and extracted with ethyl acetate-ether. The organic extract was washed with water and saturated sodium chloride solution, dried over anhydrous magnesium sulfate, filtered and concentrated to 12 g of oil. This oil was purified by flash chromatography (silica, ethyl acetate) to give 10.3 g of oil. A portion (3.5 g) of this oil was converted to the maleate salt in ethanol-ether to give 4 g of the title compound as a solid. This solid was recrystallized from ethanol-ether to give 3.5 g of solid, m.p. 155°–156° C.

ANALYSIS:

Calculated for $C_{21}H_{22}N_4O_5$: 61.46%C 5.40%H 13.65%N Found: 61.39%C 5.24%H 13.34%N

EXAMPLE 66

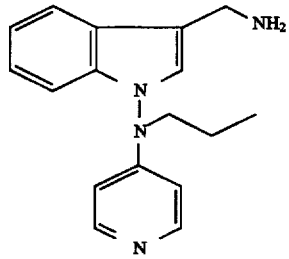

3-Aminomethyl-N-propyl-N-(4-pyridinyl)-1H-indol-1-amine dihydrochloride

A solution of N-propyl-N-(4-pyridinyl)-1H-indol-1-amine-3-carboxaldehyde oxime (5.5 g) in 100 ml 95% ethanol was quickly treated with Raney alloy (7.3 g, 50:50 Al/Ni alloy) and then with a solution of sodium hydroxide (7.8 g) dissolved in 100 ml water. The exothermic reaction which initiated was controlled with a reflux condenser. The mixture cooled to ambient temperature and stirred for two hours. The Raney alloy catalyst (pyrophoric) was removed by filtration and was washed with 50% aqueous ethanol. The filtrate was concentrated to remove the ethanol and the aqueous residue was extracted with dichloromethane. The organic extract was washed with water and saturated sodium chloride solution, dried over magnesium sulfate, filtered and concentrated to 4.7 g of oil. This was combined with 0.9 g product obtained from a trial reduction and the combined product was purified by flash chromatography (silica, 20% methanol in dichloromethane) to give 4.3 g of oil. This oil was converted to the dihydrochloride salt in methanol and the solution was concentrated to a residue. The residue was recrystallized twice from 20% methanol in acetonitrile to yield 2.9 g of the title compound as a solid, m.p. 254°–256° C.

ANALYSIS:

Calculated for $C_{17}H_2 \cdot Cl_2N_4$: 57.79%C 6.28%H 15.86%N Found: 57.69%C 6.05%H 15.85%N

EXAMPLE 67

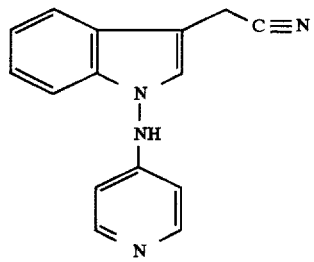

3-Cyanomethyl-N-(4-pyridinyl)-1H-indol-1-amine

3-Cyanomethyl-1H-indol-1-amine (12 g) and 4-chloropyridine hydrochloride (12 g) were combined in isopropanol (250 ml). After stirring at reflux (90° C.) for six hours, the mixture was poured into water (500 ml) and stirred five minutes. Thereafter the pH of the mixture was adjusted to 10 with sodium carbonate and the mixture was extracted with ethyl acetate (2x). The organic layer was washed with water (2x), brine, dried over anhydrous magnesium sulfate, filtered and evaporated to give an oil (22 g). This oil was eluted on a silica gel column with ethyl acetate. Fractions containing product were combined and concentrated to an oil (16 g) which solidified upon standing. A portion of this solid was recrystallized from ethanol/ether (1:20) to give the title compound as a solid (2 g), m.p. 152°–153° C.

ANALYSIS:

Calculated for $C_{19}H_{12}N_4$: 72.56%C 4.87%H 22.57%N Found: 72.41%C 4.86%H 22.16%N

EXAMPLE 68

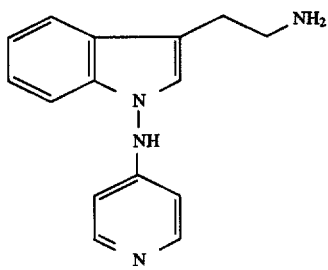

3-Aminoethyl-N-(4-pyridinyl)-1H-indol-1-amine dimaleate

To a solution of 3-cyanomethyl-N-(4-pyridinyl)-1H-indol-1-amine (3.0 g) in 95% ethanol (80 ml) was added Raney alloy (4.2 g, 50%Al/Ni) followed by the dropwise addition of an aqueous solution of sodium hydroxide (6.0 g) in water (85 ml). A mild exotherm resulted and the mixture was stirred at ambient temperature for two hours. Thereafter the mixture was filtered and the filtrate was diluted with water (100 ml). This mixture was extracted with ethyl acetate (3 x). The organic layer was washed with water (2 x) and brine, dried over anhydrous magnesium sulfate, filtered and concentrated to an oil (2.4 g). This oil was eluted on a silica column with 25% methanol/dichloromethane via flash chromatography to give a solid (2.2 g). This material was dissolved in hot ethanol, acidified to pH 1 with ethanolic maleic acid and thereafter diluted with ether. The resultant precipitate was collected and dried to give the title compound as a solid (4.2 g), m.p. 163° C. (dec)

ANALYSIS:

Calculated for $C_{15}H_{16}N_4 \cdot 2C_4H_4O_4$: 57.02%C 4.99%H 11.57%N Found: 56.87%C 5.04%H 11.42%N

EXAMPLE 69

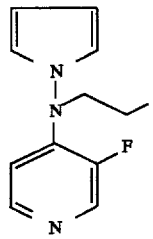

3-Fluoro-N-propyl-N-(1H-pyrrol-1-yl)-4-pyridinamine hydrochloride

A suspension of sodium hydride (0.8 g of a 60% suspension in oil washed with hexanes) in dimethylformamide (20 ml) which had been cooled to 5° C. was added to a solution of 3-fluoro-N-(1H-pyrrol-1-yl)-4-pyridinamine (3.5 g) in dimethylformamide (25 ml). After stirring at 5° C. for fifteen minutes, a solution of propyl bromide (1.8 ml) in dimethylformamide (20 ml) was added. The mixture was stirred at ambient temperature for thirty minutes. Thereafter the mixture was poured into ice-water (200 ml), stirred for five minutes and extracted with ethyl acetate. The organic layer was then washed with water and brine, dried over anhydrous magnesium sulfate, filtered and evaporated to an oil (4.0 g). This oil was eluted on a silica gel column with ethyl acetate via HPLC. The fractions containing product were evaporated to an oil (3.6 g). This oil was dissolved in ethanol (200 ml) and acidified to pH 1 with ethereal hydrogen chloride. The resultant precipitate was collected and dried to give a solid (2.5 g) , m.p. 194°–5° C.

ANALYSIS:

Calculated for $C_{12}H_{14}FN_3 \cdot HCl$: 56.36%C 5.91%H 16.43%N Found: 56.21%C 5.87%H 16.39%N

EXAMPLE 70

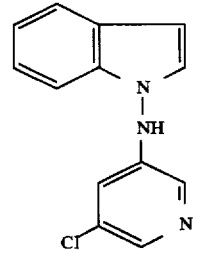

(5-Chloro-pyridin-3-yl)-1H-indol-1-amine

Potassium tert-butoxide (12.7) was added to a 0° C. solution of N-aminoindole (6.0 g) in 1-methyl-2-pyrrolidinone (150 ml). After stirring for thirty minutes, 3,5-dichloropyridine (7.5 g) was added and the resulting mixture was stirred at room temperature for five hours. The reaction mixture was quenched with water, diluted with ethyl acetate (500 ml) and washed with brine (3×500 ml). The organic layer was dried over anhydrous sodium sulfate and concentrated in vacuo to give an oil. Purification of the oil by flash chromatography (silica, 0–2% methanol/dichloromethane) afforded the title compound (11.1 g), m.p. 154°–156° C.

ANALYSIS:

Calculated for $C_{13}H_{10}ClN_3$: 64.07%C 4.14%H 14.55%Cl 17.24%N Found: 63.77%C 4.14%H 14.63%Cl 17.21%N

EXAMPLE 71

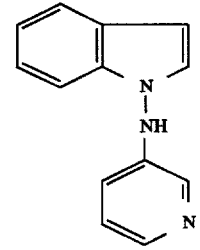

N-(3-Pyridinyl)-1H-indol-1-amine

Ten percent palladium on carbon (1.35 g) was added to a solution of (5-chloro-3-pyridinyl)-1H-indol-1-amine (5.8 g) in 3:1 ethanol/ethyl acetate (20 ml) and the resulting suspension was hydrogenated at 344.74 Kpa (50 psi, Parr shaker) for forty-eight hours at room temperature. The reaction mixture was filtered and the filter cake washed with absolute ethanol (100 ml). The filtrate was concentrated in vacuo to afford an oil. Purification of the crude product by flash chromatography (silica, 0–2.5% methanol/dichloromethane), followed by recrystallization from ether/heptane afforded the title compound as a solid (2.3 g), m.p. 127°–128° C.

47

ANALYSIS:

Calculated for $C_{13}H_{11}N_3$: 74.62%C 5.30%H 20.08%N
Found: 74.21%C 5.33%H 20.11%N

EXAMPLE 72

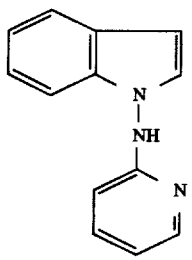

N-(2-Pyridinyl)-1H-indol-1-amine

Potassium tert-butoxide (3.4 g) was added to a room temperature solution of N-aminoindole (2.0 g) in 1-methyl-2-pyrrolidinone (40 ml). After stirring for one hour, 2-chloropyridine (1.6 ml) was added and the resulting solution was stirred for forty-eight hours. The reaction mixture was then quenched with water, diluted with ethyl acetate (250 ml) and washed with brine (3×250 ml). The organic layer was dried over anhydrous sodium sulfate and concentrated in vacuo to give an oil. Purification of the residue by flash chromatography (silica, 0–5% ethyl acetate/dichloromethane) gave the title compound as a solid (2.0 g), m.p. 109°–110° C.

ANALYSIS:

Calculated for $C_{13}H_{11}N_3$: 74.62%C 5.30%H 20.08%N
Found: 74.34%C 5.29%H 20.05%N

EXAMPLE 73

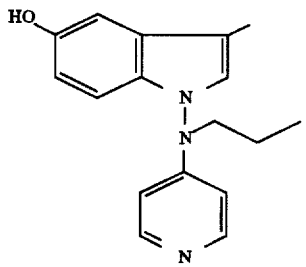

3-Methyl-1-(propyl-4-pyridinylamino)-1H-indol-5-ol hemi-oxalate

3-Methyl-5-(phenylmethoxy)-1-(propyl-4-pyridinylamino)-1H-indole (7.8 g) in absolute ethanol (275 ml) was hydrogenated at 344.74 Kpa (Parr shaker, 50 psi) over ten percent palladium on carbon (0.8 g) at 50° C. for two to three hours. The catalyst was removed by filtration and the solids were washed with methanol. The combined filtrate was concentrated and the product purified via flash column chromatography (silica, 2% triethylamine/ether) affording the product as an oil. This oil was dissolved in absolute ethanol. Thereafter one equivalent of oxalic acid which had been dissolved in absolute ethanol was added and the title compound, m.p. 235°–237° C., precipitated from solution and was collected by filtration.

ANALYSIS:

Calculated for $C_{17}H_{19}N_3O \cdot 0.5CH_2O_4H$:66.23%C 6.19%H 12.88%N Found: 65.91%C 6.33%H 12.58%N

48

EXAMPLE 74

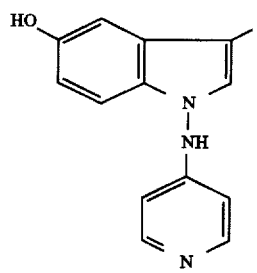

3-Methyl-1-(4-pyridinylamino)-1H-indol-5-ol

3-Methyl-5-phenylmethoxy-1-(4-pyridinylamino)-1H-indole (2.2 g) dissolved in absolute ethanol (80 ml) was hydrogenated at 344.74 Kpa (Parr shaker, 50 psi) over ten percent palladium on carbon (0.26 g) at 50° C. for two hours. The catalyst was removed by filtration and the solids were washed with methanol. Concentration and recrystallization from methanol afforded the title compound as a solid (0.5 g), m.p. 239°–241° C. (dec.).

ANALYSIS:

Calculated for $C_{14}H_{13}N_3O$: 70.28%C 5.48%H 17.56%N
Found: 69.95%C 5.46%H 17.41%N

EXAMPLE 75

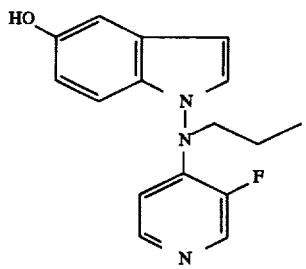

1-[Propyl-4-(3-fluoropyridinyl)amino]-1H-indol-5-ol hydrochloride

A solution of N-(3-fluoropyridin-4-yl)-5-phenylmethoxy-N-propyl-1H-indol-1-amine (15.0 g) in ethanol (200 ml) was hydrogenated at 344.74 Kpa (Parr shaker, 50 psi) over ten percent palladium on carbon (1.5 g) at 50° C. for three hours. Upon cooling, the mixture was filtered, and the filtrate evaporated to a solid (11.4 g). This material was purified by preparative HPLC chromatography [silica, ethyl acetate/dichloromethane (1:3)]. The fractions containing product were evaporated to a solid (8.5 g). A portion (2.0 g) of this material was dissolved in ethanol (50 ml). The pH was adjusted to 1 with addition of ethereal hydrogen chloride and then diluted with ether (200 ml). The resulting precipitate was collected and dried to give the title compound (2.1 g), m.p. 218° C. (dec.).

ANALYSIS:

Calculated for $C_{16}H_{16}FN_3O \cdot HCl$: 59.72%C 5.33%H 13.06%N Found: 59.30%C 5.36%H 12.62%N

EXAMPLE 76

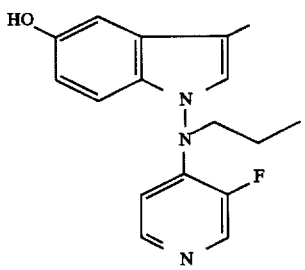

1-[(3-Fluoro-4-pyridinyl)propylamino]-3-methyl-1H-indol-5-ol

1-[(3-Fluoro-4-pyridinyl)propylamino]-3-methyl-5-(phenylmethoxy)-1H-indole (15.8 g) was dissolved in absolute ethanol (200 ml) and hydrogenated at 344.74 Kpa (Parr shaker, 50 psi) at 50° C. for seven and one-half hours. Thereafter, the mixture was filtered and the solids were washed with absolute ethanol. The combined filtrates were concentrated and the residue was purified via preparative HPLC (silica, 3:1 dichloromethane/ethyl acetate) to afford an oil (5.0 g) Addition of ethyl acetate solidified the product which was recrystallized from ethyl acetate to give a solid, m.p. 157°–160° C.

ANALYSIS:

Calculated for $C_{17}H_{18}FN_3O$: 68.21%C 6.06%H 14.04%N
Found: 67.81%C 6.09%H 13.73%N

EXAMPLE 77

N-(2,5-Dimethyl-1H-pyrrol-1-yl)-N-(n-propyl)-4-pyridinamine maleate

A solution of N-(2,5-Dimethyl-1H-pyrrol-1-yl)-4-pyridinamine (2.2 g) in dimethylformamide (20 ml) was slowly added to an ice-cooled suspension of sodium hydride (60% oil dispersion, 0.6 g washed with hexanes) in dimethylformamide (5 ml). After anion formation, a solution of 1-bromopropane (1.7 g) in dimethylformamide (5 ml) was added. After one hour the reaction mixture was quenched with ice-water and extracted with ethyl acetate. The organic extract was washed with water and brine, dried over anhydrous magnesium sulfate, filtered and evaporated to yield an oil (2.7 g). This oil was purified by flash chromatography (silica, ethyl acetate) to give an oil (2.5 g). This oil was converted to the maleate salt in methanol-ether to give the crystalline title compound (3.0 g), m.p. 133°–135° C.

ANALYSIS:

Calculated for $C_{14}H_{19}N_1 \cdot C_4H_4O_4$: 62.59%C 6.71%H 12.17%N Found: 62.58%C 6.71%H 12.10%N

What is claimed is:

1. A method of treating convulsions in a patient in need thereof which comprises administering to such a patient a convulsion alleviating amount of a compound of the formula

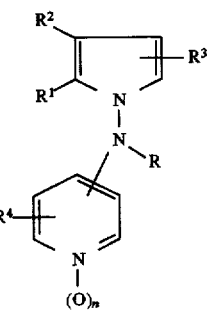

wherein

R is hydrogen, $(C_1-C_6)$alkyl, $(C_2-C_6)$alkenyl, $(C_2-C_6)$alkynyl or phenyl$(C_1-C_6)$alkyl;

$R^1$ is hydrogen, halogen or $(C_1-C_6)$alkyl;

$R^2$ is hydrogen, halogen or $(C_1-C_6)$alkyl; or $R^1$ and $R^2$ taken together with the carbons to which they are attached form a benzene ring fused to the pyrrole ring wherein the benzene ring is optionally substituted by one or two substituents independently selected from the group of halogen, $(C_1-C_6)$alkyl, $(C_1-C_6)$alkoxy, aryl $(C_1-C_6)$alkoxy, hydroxy, nitro, amino, $(C_1-C_6)$alkylamino or di $(C_1-C_6)$alkylamino;

$R^3$ is hydrogen, halogen or $(C_1-C_6)$alkyl;

$R^4$ is hydrogen, halogen, amino or $(C_1-C_6)$alkyl;

n is 0 or 1; or a pharmaceutically acceptable acid addition salt thereof.

2. The method of claim 1 wherein the compound has the formula

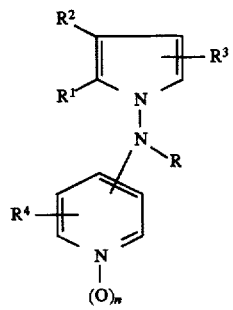

wherein

R is hydrogen, $(C_1-C_6)$alkyl, $(C_2-C_6)$alkenyl, $(C_2-C_6)$alkynyl or phenyl$(C_1-C_6)$alkyl;

$R^1$ is hydrogen, halogen or $(C_1-C_6)$alkyl;

$R^2$ is hydrogen, halogen or $(C_1-C_6)$alkyl;

$R^3$ is hydrogen, halogen or $(C_1-C_6)$alkyl;

$R^4$ is hydrogen, halogen, amino or $(C_1-C_6)$alkyl;

n is 0 or 1; or a pharmaceutically acceptable acid addition salt thereof.

3. The method of claim 2 wherein $R^2$ and $R^3$ are hydrogen, $R^4$ is hydrogen or $(C_1-C_6)$alkyl and n is 0.

4. A method of treating convulsions in a patient in need thereof which comprises administering to such a patient a convulsion alleviating amount of a compound of the formula

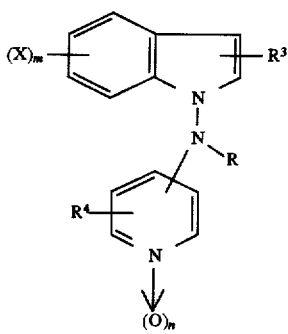

wherein

R is hydrogen, (C$_1$–C$_6$)alkyl, (C$_2$–C$_6$)alkenyl, (C$_2$–C$_6$) alkynyl or phenyl(C$_1$–C$_6$)alkyl;

R$^1$ is hydrogen, halogen or (C$_1$–C$_6$)alkyl;

R$^3$ is hydrogen, halogen, (C$_1$–C$_6$)alkyl or (CH$_2$)$_z$NH$_2$;

R$^4$ is hydrogen, halogen, amino or (C$_1$–C$_6$)alkyl;

m is 1 or 2;

n is 0 or 1; and z is 1 or 2; or a pharmaceutically acceptable acid addition salt thereof.

5. The method of claim 4 wherein X is hydrogen, R$^3$ is hydrogen or methyl, R$^4$ is hydrogen or fluoro and n is 0.

6. The method of claim 1 wherein the compound is N-(1H-pyrrol-1-yl)-4-pyridinamine or a pharmaceutically acceptable acid addition salt thereof.

7. The method of claim 1 wherein the compound is N-methyl-N-(1H-pyrrol-1-yl)-4-pyridinamine or a pharmaceutically acceptable acid addition salt thereof.

8. The method of claim 1 wherein the compound is N-ethyl-N-(1H-pyrrol-1-yl)-4-pyridinamine or a pharmaceutically acceptable acid addition salt thereof.

9. The method of claim 1 wherein the compound is N-propyl-N-(1H-pyrrol-1-yl)-4-pyridinamine or a pharmaceutically acceptable acid addition salt thereof.

10. The method of claim 1 wherein the compound is N-phenylmethyl-N-(1H-pyrrol-1-yl)-4-pyridinamine or a pharmaceutically acceptable acid addition salt thereof.

11. The method of claim 1 wherein the compound is N-(butyl)-N-(1H-pyrrol-1-yl)-4-pyridinamine or a pharmaceutically acceptable acid addition salt thereof.

12. The method of claim 1 wherein the compound is N-(2-propenyl)-N-(1H-pyrrol-1-yl)-4-pyridinamine or a pharmaceutically acceptable acid addition salt thereof.

13. The method of claim 1 wherein the compound is N-(2-propynyl)-N-(1H-pyrrol-1-yl)-4-pyridinamine or a pharmaceutically acceptable acid addition salt thereof.

14. The method of claim 1 wherein the compound is N-(2-chloro-1H-pyrrol-1-yl)-N-methyl-4-pyridinamine or a pharmaceutically acceptable acid addition salt thereof.

15. The method of claim 1 wherein the compound is N-(2-chloro-1H-pyrrol-1-yl)-N-ethyl-4-pyridinamine or a pharmaceutically acceptable acid addition salt thereof.

16. The method of claim 1 wherein the compound is N-(2-chloro-1H-pyrrol-1-yl)-N-propyl-4-pyridinamine or a pharmaceutically acceptable acid addition salt thereof.

17. The method of claim 1 wherein the compound is N-(2-chloro-1H-pyrrol-1-yl)-4-pyridinamine or a pharmaceutically acceptable acid addition salt thereof.

18. The method of claim 1 wherein the compound is 2-butyl-N-methyl-N-(1H-pyrrol-1-yl)-4-pyridinamine or a pharmaceutically acceptable acid addition salt thereof.

19. The method of claim 1 wherein the compound is N-(2-ethyl-1H-pyrrol-1-yl)-N-methyl-4-pyridinamine or a pharmaceutically acceptable acid addition salt thereof.

20. The method of claim 1 wherein the compound is N-methyl-N-(2-propyl-1H-pyrrol-1-yl)-4-pyridinamine or a pharmaceutically acceptable acid addition salt thereof.

21. The method of claim 1 wherein the compound is N-(4-pyridinyl)-1H-indol-1-amine or a pharmaceutically acceptable acid addition salt thereof.

22. The method of claim 1 wherein the compound is N-methyl-N-(4-pyridinyl)-1H-indol-1-amine or a pharmaceutically acceptable acid addition salt thereof.

23. The method of claim 1 wherein the compound is N-ethyl-N-(4-pyridinyl)-1H-indol-1-amine or a pharmaceutically acceptable acid addition salt thereof.

24. The method of claim 1 wherein the compound is N-propyl-N-(4-pyridinyl)-1H-indol-1-amine or a pharmaceutically acceptable acid addition salt thereof.

25. The method of claim 1 wherein the compound is 5-ethoxy-N-propyl-N-(4-pyridinyl)-1H-indol-1-amine or a pharmaceutically acceptable acid addition salt thereof.

26. The method of claim 1 wherein the compound is 3-ethenyl-N-methyl-N-(4-pyridinyl)-1H-indol-1-amine or a pharmaceutically acceptable acid addition salt thereof.

27. The method of claim 1 wherein the compound is 3-ethyl-N-methyl-N-(4-pyridinyl)-1H-indol-1-amine or a pharmaceutically acceptable acid addition salt thereof.

28. The method of claim 1 wherein the compound is 5-chloro-N-(4-pyridinyl)-1H-indol-1-amine or a pharmaceutically acceptable acid addition salt thereof.

29. The method of claim 1 wherein the compound is 5-chloro-N-propyl-N-(4-pyridinyl)-1H-indol-1-amine or a pharmaceutically acceptable acid addition salt thereof.

30. The method of claim 1 wherein the compound is 5-bromo-N-(4-pyridinyl)-1H-indol-1-amine or a pharmaceutically acceptable acid addition salt thereof.

31. The method of claim 1 wherein the compound is 5-bromo-N-methyl-N-(4-pyridinyl)-1H-indol-1-amine or a pharmaceutically acceptable acid addition salt thereof.

32. The method of claim 1 wherein the compound is 5-bromo-N-propyl-N-(4-pyridinyl)-1H-indol-1-amine or a pharmaceutically acceptable acid addition salt thereof.

33. The method of claim 1 wherein the compound is 5-nitro-N-(4-pyridinyl)-1H-indol-1-amine or a pharmaceutically acceptable acid addition salt thereof.

34. The method of claim 1 wherein the compound is N-ethyl-5-nitro-N-(4-pyridinyl)-1H-indol-1-amine or a pharmaceutically acceptable acid addition salt thereof.

35. The method of claim 1 wherein the compound is 3-ethyl-N-(4-pyridinyl)-1H-indol-1-amine or a pharmaceutically acceptable acid addition salt thereof.

36. The method of claim 1 wherein the compound is 3-ethyl-N-propyl-N-(4-pyridinyl)-1H-indol-1-amine or a pharmaceutically acceptable acid addition salt thereof.

37. The method of claim 1 wherein the compound is N-(3-fluoro-4-pyridinyl)-3-methyl-1H-indol-1-amine or a pharmaceutically acceptable acid addition salt thereof.

38. The method of claim 1 wherein the compound is N-(3-fluoro-4-pyridinyl)-N-propyl-3-methyl-1H-indol-1-amine or a pharmaceutically acceptable acid addition salt thereof.

39. The method of claim 1 wherein the compound is N-(3-fluoro-4-pyridinyl)-N-propyl-1H-indol-1-amine or a pharmaceutically acceptable acid addition salt thereof.

40. The method of claim 1 wherein the compound is 2-methyl-N-(4-pyridinyl)-1H-indol-1-amine or a pharmaceutically acceptable acid addition salt thereof.

41. The method of claim 1 wherein the compound is N-(3-methyl-4-pyridinyl)-1H-indol-1-amine or a pharmaceutically acceptable acid addition salt thereof.

42. The method of claim 1 wherein the compound is N-(3-ethyl-4-pyridinyl)-N-propyl-1H-indol-1-amine or a pharmaceutically acceptable acid addition salt thereof.

43. The method of claim 1 wherein the compound is N-(3-fluoro-4-pyridinyl)-1H-indol-1-amine or a pharmaceutically acceptable acid addition salt thereof.

44. The method of claim 1 wherein the compound is N-(3-chloro-4-pyridinyl)-1H-indol-1-amine or a pharmaceutically acceptable acid addition salt thereof.

45. The method of claim 1 wherein the compound is N-(3-(fluoro-4-pyridinyl)-2-methyl-1H-indol-1-amine or a pharmaceutically acceptable acid addition salt thereof.

46. The method of claim 1 wherein the compound is N-(3-chloro-4-pyridinyl)-3-methyl-1H-indol-1-amine or a pharmaceutically acceptable acid addition salt thereof.

47. The method of claim 1 wherein the compound is N-propyl-N-(4-pyridinyl)-3-ethenyl-1H-indol-1-amine or a pharmaceutically acceptable acid addition salt thereof.

48. The method of claim 1 wherein the compound is 3-ethyl-N-propyl-N-(4-pyridinyl)-1H-indol-1-amine or a pharmaceutically acceptable acid addition salt thereof.

49. The method of claim 1 wherein the compound is N-butyl-N-(4-pyridinyl)-1H-indol-1-amine or a pharmaceutically acceptable acid addition salt thereof.

50. The method of claim 1 wherein the compound is N-(2-propynyl)-N-(4-pyridinyl)-1H-indol-1-amine or a pharmaceutically acceptable acid addition salt thereof.

51. The method of claim 1 wherein the compound is N-(2-methylpropyl)-N-(4-pyridinyl)-1H-indol-1-amine or a pharmaceutically acceptable acid addition salt thereof.

52. The method of claim 1 wherein the compound is N-pentyl-N-(4-pyridinyl)-1H-indol-1-amine or a pharmaceutically acceptable acid addition salt thereof.

53. The method of claim 1 wherein the compound is N-(1-methylpropyl)-N-(4-pyridinyl)-1H-indol-1-amine or a pharmaceutically acceptable acid addition salt thereof.

54. The method of claim 1 wherein the compound is N-(1-methylethyl)-N-(4-pyridinyl)-1H-indol-1-amine or a pharmaceutically acceptable acid addition salt thereof.

55. The method of claim 1 wherein the compound is 2-methyl-N-propyl-N-(4-pyridinyl)-1H-indol-1-amine or a pharmaceutically acceptable acid addition salt thereof.

56. The method of claim 1 wherein the compound is N-(3-fluoro-4-pyridinyl)-N-(2-propenyl)-3-methyl-1H-indol-1-amine or a pharmaceutically acceptable acid addition salt thereof.

57. The method of claim 1 wherein the compound is N-(3-chloro-4-pyridinyl)-N-propyl-1H-indol-1-amine or a pharmaceutically acceptable acid addition salt thereof.

58. The method of claim 1 wherein the compound is N-(3-fluoro-4-pyridinyl)-N-(2-propynyl)-1H-indol-1-amine or a pharmaceutically acceptable acid addition salt thereof.

59. The method of claim 1 wherein the compound is N-(3-fluoro-4-pyridinyl)-3-methyl-N-(2-propynyl)-1H-indol-1-amine or a pharmaceutically acceptable acid addition salt thereof.

60. The method of claim 1 wherein the compound is N-(3-fluoro-4-pyridinyl)-2-methyl-N-propyl-1H-indol-1-amine or a pharmaceutically acceptable acid addition salt thereof.

61. The method of claim 1 wherein the compound is N-(3-chloro-4-pyridinyl)-3-methyl-N-propyl-1H-indol-1-amine or a pharmaceutically acceptable acid addition salt thereof.

62. The method of claim 1 wherein the compound is N-(3-fluoro-4-pyridinyl)-N-(2-propenyl)-1H-indol-1-amine or a pharmaceutically acceptable acid addition salt thereof.

63. The method of claim 1 wherein the compound is 4-[N-(1H-indol-1-yl)]-3,4-pyridinamine or a pharmaceutically acceptable acid addition salt thereof.

64. The method of claim 1 wherein the compound is 3-chloro-N-(4-pyridinyl)-1H-indol-1-amine or a pharmaceutically acceptable acid addition salt thereof.

65. The method of claim 1 wherein the compound is 3-chloro-N-propyl-N-(4-pyridinyl)-1H-indol-1-amine or a pharmaceutically acceptable acid addition salt thereof.

66. The method of claim 4 wherein the compound is 3-aminomethyl-N-propyl-N-(4-pyridinyl)-1H-indol-1-amine, or a pharmaceutically acceptable acid addition salt thereof.

67. The method of claim 4 wherein the compound is 3-aminoethyl-N-(4-pyridinyl)-1H-indol-1-amine or a pharmaceutically acceptable acid addition salt thereof.

68. The method of claim 1 wherein the compound is 1-[propyl-4-(3-fluoropyridinyl)amino]-1H-indol-5-ol or a pharmaceutically acceptable acid addition salt thereof.

69. The method of claim 1 wherein the compound is 3-methyl-1-(4-pyridinylamino)-1H-indol-5-ol or a pharmaceutically acceptable acid addition salt thereof.

70. The method of claim 1 wherein the compound is 3-methyl-1-(propyl-4-pyridinylamino)-1H-indol-5-ol or a pharmaceutically acceptable acid addition salt thereof.

71. The method of claim 1 wherein the compound is N-(3-pyridinyl)-1H-indol-1-amine, or a pharmaceutically acceptable acid addition salt thereof.

72. The method of claim 1 wherein the compound is N-(2-pyridinyl)-1H-indol-1-amine or a pharmaceutically acceptable acid addition salt thereof, or.

73. The method of claim 1 wherein the compound is 3-fluoro-N-propyl-N-(1H-pyrrol-1-yl)-4-pyridinamine or a pharmaceutically acceptable acid addition salt thereof.

74. The method of claim 1 wherein the compound is 1-[(3-fluoro-4-pyridinyl)propylamino]-3-methyl-1H-indol-5-ol or a pharmaceutically acceptable acid addition salt thereof.

75. The method of claim 1 wherein the compound is N-(2,5-dimethyl-1H-pyrrol-1-yl)-N-(n-propyl)-4-pyridinamine or a pharmaceutically acceptable acid addition salt thereof.

76. A pharmaceutical composition which comprises a pharmaceutically acceptable carrier and an effective anticonvulsant amount of a compound of the formula

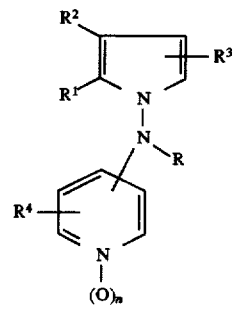

wherein

R is hydrogen, $(C_1-C_6)$alkyl, $(C_2-C_6)$alkenyl, $(C_2-C_6)$alkynyl or phenyl$(C_1-C_6)$alkyl;

$R^1$ is hydrogen, halogen or $(C_1-C_6)$alkyl;

$R^2$ is hydrogen, halogen, or $(C_1-C_6)$alkyl;

$R^3$ is hydrogen, halogen or $(C_1-C_6)$alkyl;

$R^4$ is hydrogen, halogen, amino or $(C_1-C_6)$alkyl; and n is 0 or 1; or a pharmaceutically acceptable acid addition salt thereof.

* * * * *